(12) United States Patent
Ibrahim

(10) Patent No.: US 12,089,661 B2
(45) Date of Patent: *Sep. 17, 2024

(54) BODY SHAPE ENHANCING APPARATUS AND METHOD

(71) Applicant: Armani Ibrahim, Staten Island, NY (US)

(72) Inventor: Armani Ibrahim, Staten Island, NY (US)

(73) Assignee: Armani Ibrahim, Staten Island, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/132,901

(22) Filed: Apr. 10, 2023

(65) Prior Publication Data

US 2023/0346048 A1 Nov. 2, 2023

Related U.S. Application Data

(63) Continuation of application No. 17/562,542, filed on Dec. 27, 2021, now Pat. No. 11,647,797, which is a continuation-in-part of application No. 29/816,996, filed on Nov. 27, 2021, now Pat. No. Des. 992,859, and a continuation-in-part of application No. 29/761,650, filed on Dec. 10, 2020, now Pat. No. Des. 942,119.

(60) Provisional application No. 63/130,661, filed on Dec. 26, 2020.

(30) Foreign Application Priority Data

Jun. 10, 2021 (CN) .................. 202130358755.X

(51) Int. Cl.
*A41B 9/00* (2006.01)

(52) U.S. Cl.
CPC .................. *A41B 9/004* (2013.01)

(58) Field of Classification Search
CPC ...................................... A41B 9/004
USPC ............................................. 2/402
See application file for complete search history.

(56) References Cited

U.S. PATENT DOCUMENTS

| | | |
|---|---|---|
| 2,534,934 A | 12/1950 | Viniegra |
| 3,084,692 A | 4/1963 | Atkinson |
| 6,360,375 B1 | 3/2002 | Hart |
| 6,997,915 B2 | 2/2006 | Gell et al. |
| 7,081,036 B1 | 7/2006 | Howard et al. |
| 8,915,899 B2 | 12/2014 | Dieringer |

(Continued)

FOREIGN PATENT DOCUMENTS

| | | |
|---|---|---|
| EP | 1269952 A2 | 1/2003 |
| EP | 1424051 | 6/2004 |

(Continued)

*Primary Examiner* — Gloria M Hale

(57) ABSTRACT

A body shape enhancing apparatus for creating a space between the thighs and simultaneously providing multiple shape enhancements is described. The body shape enhancing apparatus comprises an outer shell casing comprising a top outer shell casing, a bottom outer shell casing, a front section, a middle section and rear section. The outer shell casing body is configured to cover a wearers undercarriage from the pelvic area to about the anus. The rear section comprises a protrusion from a top of the rear base section, the protrusion supported by a similar shape internal support protrusion.

29 Claims, 20 Drawing Sheets

(56) References Cited

U.S. PATENT DOCUMENTS

| | | |
|---|---|---|
| D751,269 S | 3/2016 | Jones |
| 11,647,797 B2 * | 5/2023 | Ibrahim ............ A61F 13/47218 2/402 |
| 2014/0165265 A1 | 6/2014 | Tulin et al. |
| 2015/0196068 A1 | 7/2015 | Tulin et al. |

FOREIGN PATENT DOCUMENTS

| | | |
|---|---|---|
| EP | 1357 875 B1 | 4/2005 |
| KR | 101061139 B1 | 8/2011 |
| WO | WO 2014/130218 | 8/2014 |

* cited by examiner

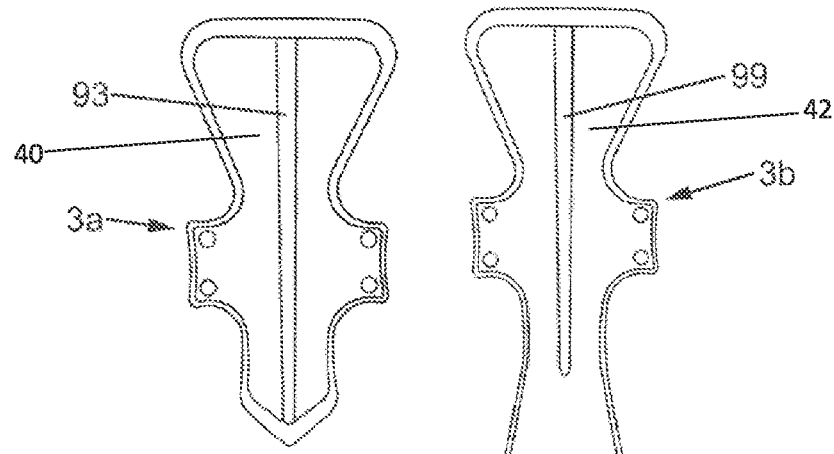
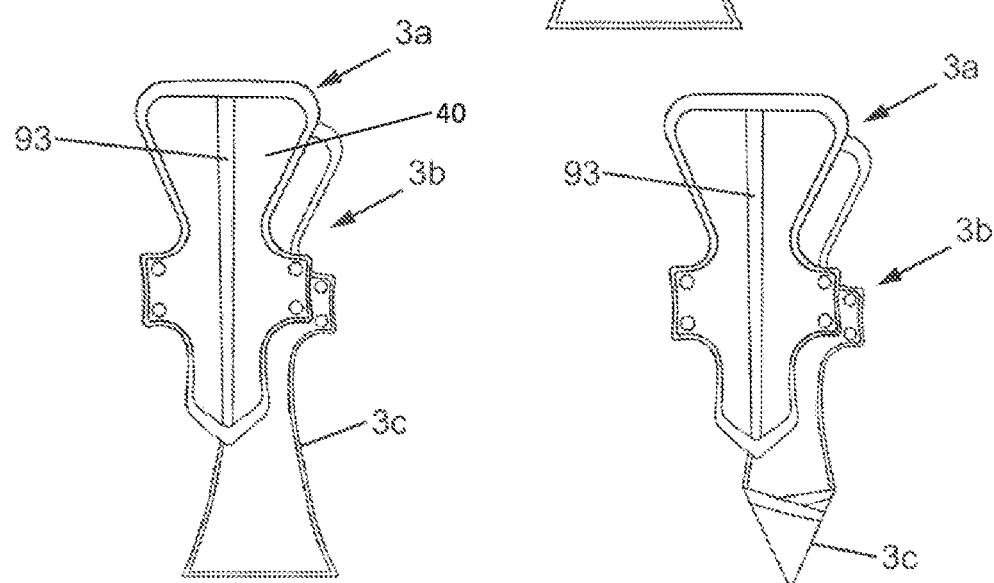
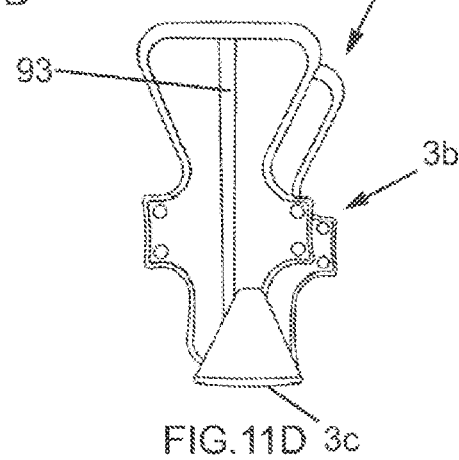

ND METHOD

BODY SHAPE ENHANCING APPARATUS AND METHOD

This application is a continuation of and claims the benefit of U.S. Non-Provisional application Ser. No. 17/562,542, filed on Dec. 27, 2021, titled BODY SHAPE ENHANCING APPARATUS AND METHOD, which issued as U.S. patent Ser. No. 11/647,797 on May 16, 2023, and is incorporated by reference herein in its entirety and further claims the benefit of U.S. Provisional Patent Application No. 63/130,661, filed on Dec. 26, 2020, titled BODY SHAPE ENHANCING APPARATUS AND METHOD, which is incorporated by reference herein in its entirety; and is a continuation in part of and claims the benefit of U.S. Design patent application No. 29/761,650, filed on Dec. 10, 2020, titled BODY SHAPE ENHANCING APPARATUS; which issued as U.S. Pat. No. D942,119 on Feb. 1, 2022, which is incorporated herein its entirety and is a continuation in part of and further claims the benefit of U.S. Design patent application No. 29/816,996, filed on Nov. 27, 2021, titled BODY SHAPE ENHANCING APPARATUS, which is currently pending and, which is incorporated herein its entirety; and claims the benefit of Chinese design Application No. ZL202130358755.X filed on Jun. 19, 2021, which is incorporated by reference herein in its entirety.

BACKGROUND OF THE INVENTION

The present disclosure relates generally to devices for enhancing the shape of a person's lower body, and more particularly to all-in-one devices providing multiple body shape enhancements, including but not limited to the creation of a thigh gap.

A strong need exits for women to have alternative body shaping and enhancing products to traditional underwear, and girdles. Studies have shown that the majority of women and girls are dissatisfied with their bodies. In many instances, this dissatisfaction leads to body shape insecurities and a focus on obtaining a desired body shape and or physical and appearance enhancement. This dissatisfaction may be the result of the lack of certain physical body features, or having a problem area or condition, and/or body shape challenges which may include, but are not limited to, overlapping, touching and/or sagging thighs, lack of a defined thigh gap, visible genital protrusion, sagging posterior such as flat buttocks or gluteal ptosis, genu valgum (knock knees), hip or apron belly bulges, thigh or hip cellulite, disproportionate body shape.

Undergarments and shapewear configured to help with enhancing body shape are well known in the art. However, these known devices have often proven to be less effective than desired and often times produce unnatural look, ineffective, bulky, uncomfortable results to the wearer's lower body when worn under clothes or as undergarments. Further, these known devices are often unable to address more than one body shape challenge at a time and may induce moisture build up due to lack of ventilation, oftentimes compelling the wearer to wear ineffective shaping products and/or several different shaping devices at the same time to try to piece together a makeshift solution for themselves, often with undesired results and dissatisfaction.

Attempts to conform to the attractiveness standards set forth by society are common, however, many of these attractiveness standards are not naturally obtainable for the majority. To meet these standards, individuals may often resort to the use of unconventional and possibly even unhealthy methods in attempting to transform their appearance. Primarily women and girls desire to achieve something called a thigh gap, which is typically an open space, or tunnel, which may be an equilateral or triangular shaped thigh gap, or any shape or size gap or space, opening or gap between the upper thighs directly underneath the crotch and buttocks region. Many, if not most, women and girls do not have a thigh gap, or space or any opening, yet highly desire it. Further some individuals have knees that curve in and are not aligned with their legs or may suffer from knock knees, overlapping thighs or not it or the like, which can prevent any opening, space and or gap between or beneath the thighs, under the crotch and buttocks. Many women and girls also experience genital protrusion through clothing, which is commonly referred to as "camel toe". This genital protrusion is often the result of constricting garments that are forked at the legs. Current genital protrusion concealment products provide little improvement, are uncomfortable to wear, don't stay in place, or are visible through certain clothing, among other issues.

Known shapewear products, which may be in the form of underwear, girdles, banding products, compression products, and the like, do not generally address the aforementioned physical or appearance concerns, wants, needs and challenges in an effective manner, especially when worn under tight or form fitting clothing. These products may cause unwanted effects such as bulges, panty lines, unflattering seam lines, squishing of the buttocks, all of which are visible through the wearer's clothing. Wearers may also feel constricted as a result of the tightness, or configuration of these products.

The failure and inability of existing options in the shapewear, undergarment, and garment industries to satisfy or solve these problems or to offer a different yet effective way to obtain certain desired body shape enhancements has left the public with a yearning for a better and/or all-in-one solution. Accordingly, there exists an unsolved need for a new and improved body shape enhancing apparatus for creating a thigh gap, lifting the buttocks, thighs and/or undercarriage (the undercarriage being the crotch area beginning from the front pelvic area and ending about the anus), and eliminating genital protrusion.

BRIEF SUMMARY OF THE INVENTION

The present disclosure relates to a body shape enhancing apparatus for creating a space between the thigh and or underneath the crotch area, and below the buttocks, while lifting, firming, and separating the buttocks and improving the volume and shape of a wearer's posterior. The body shaping or shape enhancing apparatus lifts and separates the thighs to enhance the appearance, shape, and silhouette of a wearer's lower body and overall shape. The body shape enhancing apparatus provides genital protrusion concealment to aid in modesty and improves the appearance of unwanted rippling and/or dimpling from cellulite in the outer hip region. The body shape enhancing apparatus may be worn with or without an undergarment or be incorporated into or attached to an undergarment or any forked article of clothing, or device. The body shape enhancing apparatus may be worn underneath or incorporated into an item of clothing, including but not limited to, shaping briefs, girdles, panties, foundation garments, hosiery, shapewear garments, activewear, leggings, swimwear, thong body suits, leotard, belt, unitard, lingerie, garters and straps, swimwear, leggings, tights, jeans, pants, jumpsuit, skirts, dresses, singlet, leotard, bodysuit, underwear straps, knitted and or sewn articles of fabrication, over the neck mankini, or over the shoulder underwear, or any article of attire or fabrication worn about the crotch.

The body shape enhancing apparatus can be made from an array of materials and may or may not comprise of several internal parts that will be discussed in greater detail in the detailed description. Body shape enhancing apparatus may comprise of an elongated or curved body, wherein the elongated body gradually narrows, and may thicken into a preferably triangular-shaped rear protrusion. In embodiments any shaped protrusion may be used. The body shaping apparatus provides the wearer with shaping support by separating the wearer's buttocks cheeks so that the buttocks may appear firmer, larger, and lifted. Additionally, the body shaping apparatus provides the wearer with genital protrusion concealment by providing an undetectable concealment barrier between the wearer's genitalia and their outer garment or undergarment, as to create the perfect seamless canvas underneath the undergarment and/or garment of wearer. When in use, the body shaping apparatus applies force at the wearer's inner groin, pelvic region, undercarriage, and between the buttocks cheeks, causing the inner groin and buttocks cheeks to push apart resulting in a lifting effect on the buttocks cheeks, hips and inner thighs, making them shapelier, lifted, and spread apart.

Body shape enhancing apparatus may or may not include one or more lateral fasteners to assist in securing the apparatus in place while worn with any undergarment or any article of clothing which makes contact with the crotch of the wearer. In other embodiments body shape enhancing apparatus may not need to use lateral fasteners to secure it and lateral fasteners would just come together underneath the wearer's crotch and garment if no undergarment s worn and may use other known means of securement in the art in a different way. These and other features and advantages of the present invention will become apparent from the following description, drawings, and claims.

BRIEF DESCRIPTION OF THE DRAWINGS

Embodiments of the present invention will be described by way of example only, and not limitation, with reference to the accompanying drawings. The drawings are not necessarily drawn to scale and wherever possible, the same or like reference numbers are used throughout the drawings to refer to the same or like parts.

FIG. 11A is a top elevational view of the disassembled outer shell casing in accordance with embodiments of the present disclosure;

FIG. 11B is a top elevational view of the disassembled outer shell casing in accordance with embodiments of the present disclosure with the top outer shell casing layered on top of the bottom outer shell casing;

FIG. 11C is a top elevational view of the disassembled outer shell casing in accordance with embodiments of the present disclosure with the rear outer shell casing folded up and positioned for receiving the internal protrusion support member 11;

FIG. 11D is a top elevational view of the disassembled outer shell casing in accordance with embodiments of the present disclosure with the rear outer shell casing back outer shell casing folded up and over positioned for receiving the internal protrusion support member;

DETAILED DESCRIPTION

Figure 1A:
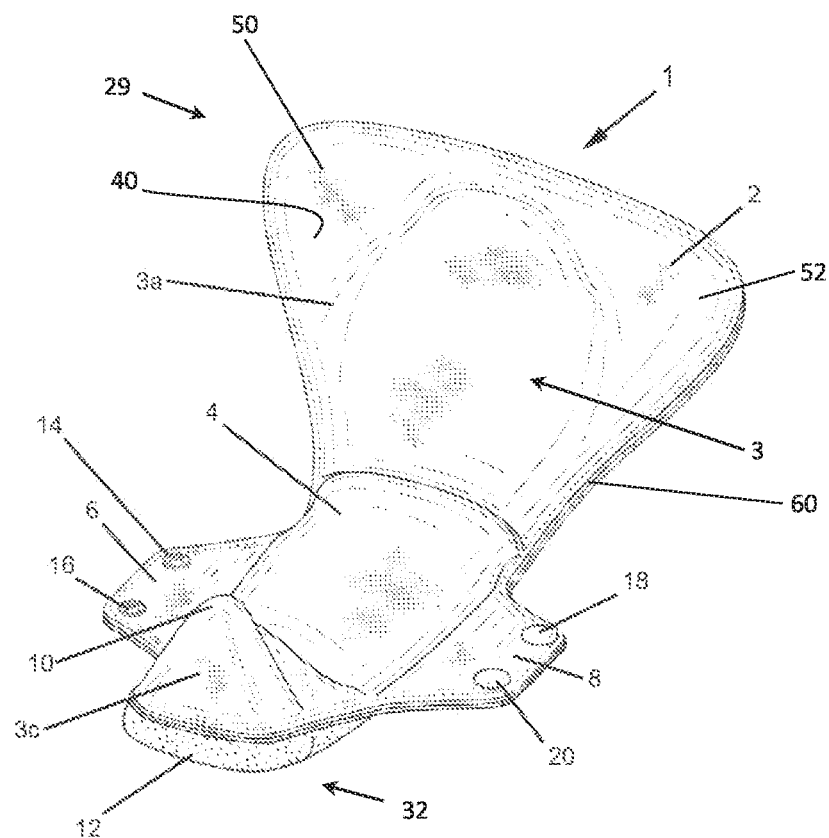
FIG. 1A is a top, left and rear perspective view of a body shape enhancing apparatus in accordance with embodiments of the present disclosure.

In the following description, like reference characters denote like or corresponding parts throughout the several views. Also in the description, it is to be understood that terms used to identify parts of the present disclosure are words of convenience and are not to be construed as limiting terms. Certain modifications and improvements will occur to those skilled in the art upon reading the foregoing description. It should be understood that all such modifications and improvements have been deleted herein for the sake of conciseness and readability but are properly within the scope of the following claims. The present disclosure is described in enabling detail in the following examples, which may represent more than one embodiment of the present disclosure.

Embodiments of the present disclosure relate to a body shape enhancing apparatus 1 for enhancing the body shape and improving the body challenges affecting a wearer's lower body through the capability of creation of an inner thigh space or gap, firming, lifting, separating the buttocks, and improving the appearance of the hip region. Further, the body shape enhancing apparatus 1 conceals genital protrusion, creates a thigh brow, which is a crease between your thigh and your hip that appears when you sit or kneel down and enhances and defines the overall lower body shape of the wearer's silhouette. Body shape enhancing apparatus 1 may be incorporated into or onto any existing undergarment or garment, or it may be manufactured and sold as an undergarment or garment with body shape enhancing apparatus 1 embedded within.

In one or more embodiment of the present disclosure body shape enhancing apparatus 1 is preferably comprised of an elongated and or cured body that can be placed at or removed from the crotch and buttocks area of a wearer at any time without the wearer needing to remove their clothing or undergarment; and in one or more embodiments is comprising of several supporting internal parts, such as a flexible supporter 22 at its core which enables the body shape enhancing apparatus to automatically cradle, hug and adhere snuggly to the wearer's undercarriage. However, in some embodiments there may be at least one supporting internal part or there may be none. The supporting internal parts may be secured in place by attachment means in the art such as using sewing or stitching, or adhesive, but not limited to any type of securement, and may be unsecured.

Figure 1B:
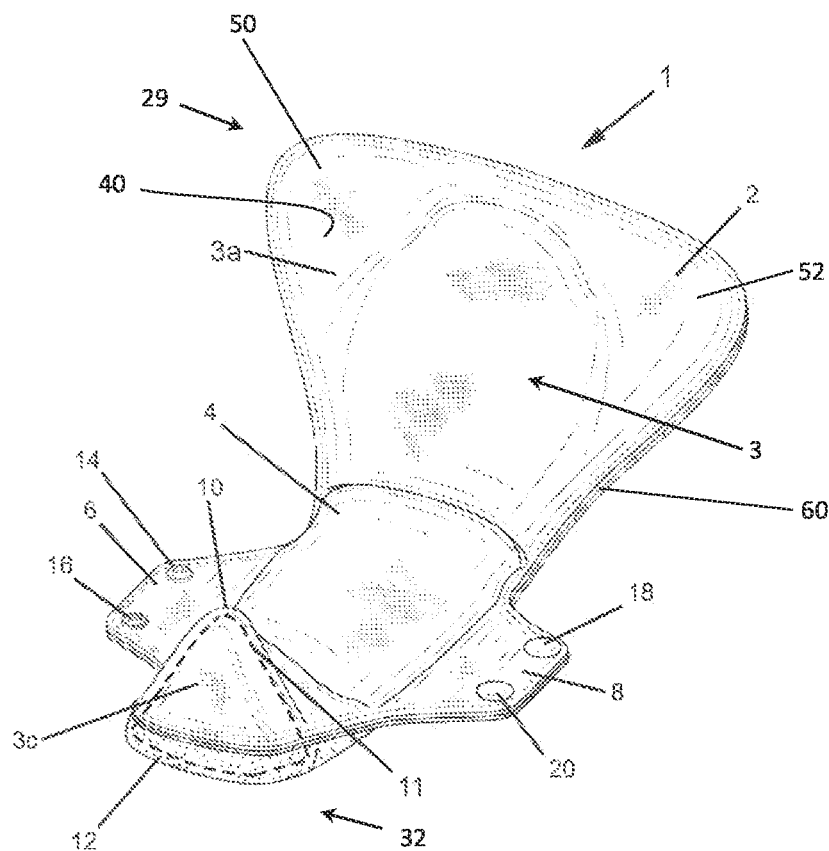
FIG. 1B is a top, left and rear perspective view of the body shape enhancing apparatus of FIG. 1A, with examples of inner structure shown by dashed lines in accordance with embodiments of the present disclosure.
Figure 2:
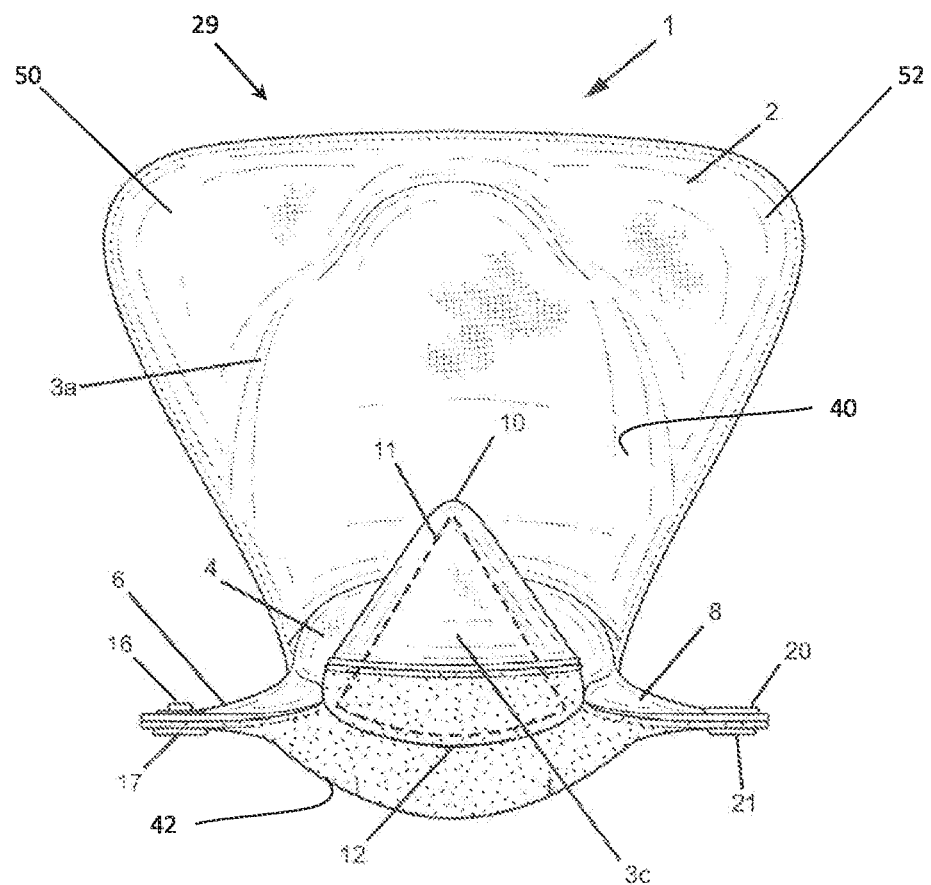
FIG. 2 is a rear elevational view of a body shape enhancing apparatus in accordance with embodiments of the present disclosure.

Turning now to the figures, FIGS. 1A, 1B and 2 show perspective views of the body shape enhancing apparatus 1 in accordance with embodiments of the present disclosure, comprising an elongated body comprising of a wide, flat pelvic front section 2 that extends from a front end 29 and thickens in depth and narrows in width toward a rear section 7 which includes rear base section 12 and terminates at rear end 32, wherein the rear base section 12 comprises a protrusion 10. The elongated body having an outer shell casing 3 that includes a top outer casing 3a having a top surface 40 affixed to a bottom outer casing 3b having a bottom surface 42 along an outer circumferential side 60, and a rear outer casing 3c. which covers the protrusion and encases an internal protrusion support member 11 that forms protrusion 10.

Figure 3:
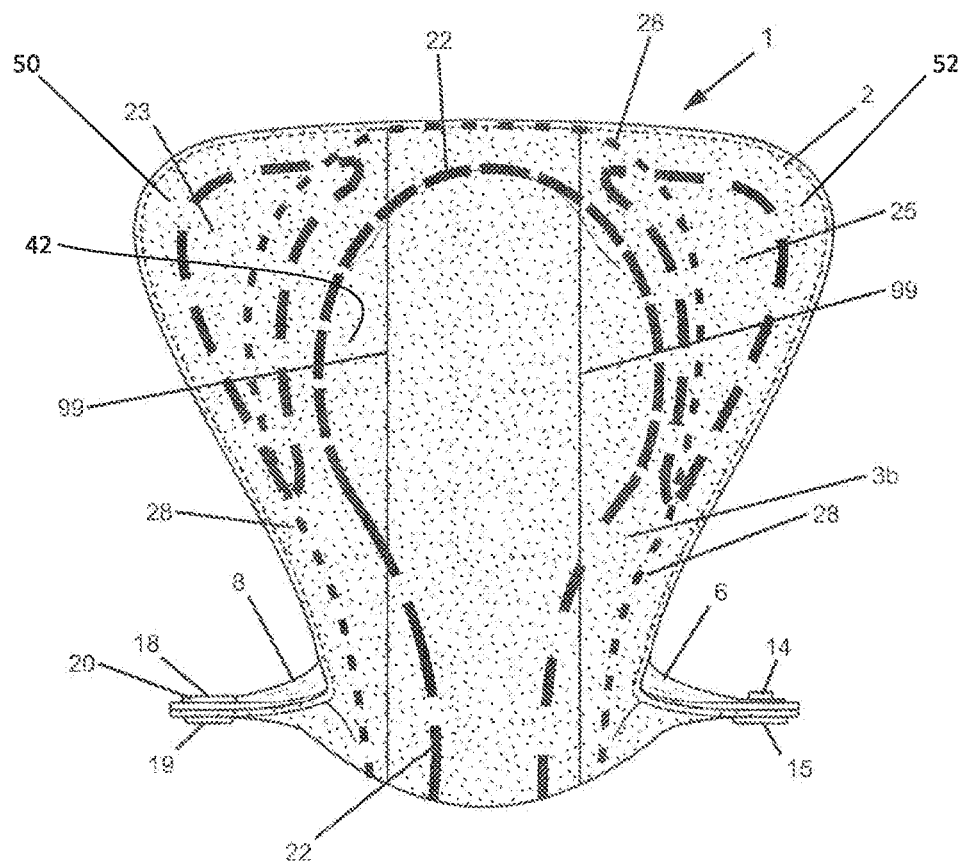
FIG. 3 is a front elevational view of body shape enhancing apparatus in accordance with embodiments of the present disclosure, with examples of inner structure shown by dashed lines in accordance with embodiments of the present disclosure.
Figure 4:
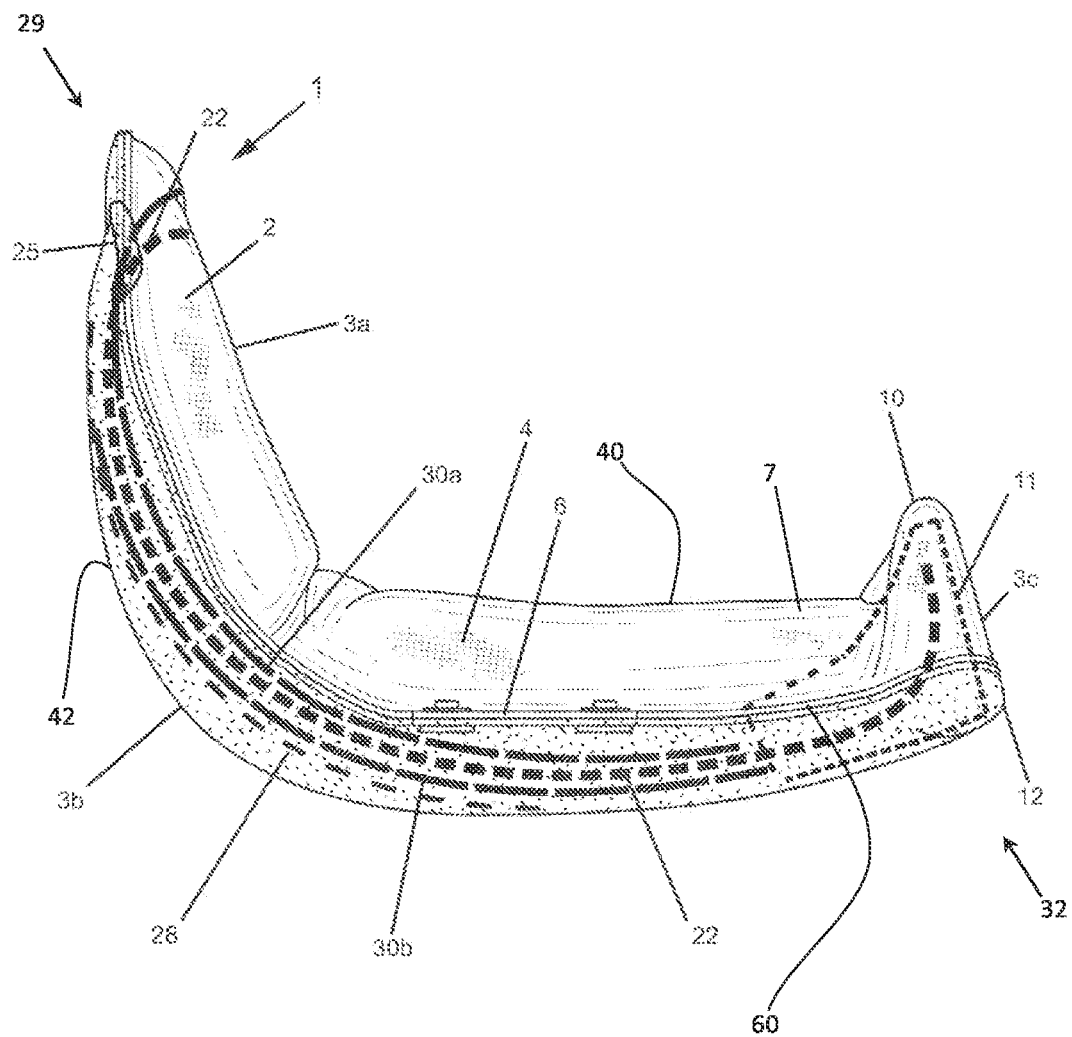
FIG. 4 is a right-side elevational view of the body shape enhancing apparatus, with examples of inner structure shown by dashed lines in accordance with embodiments of the present disclosure.

FIGS. 3 and 4 show front and side views, respectively, of the body shaping apparatus 1 in accordance with embodiments of the present disclosure, showing examples of internal structural elements in dashed lines. The internal structural elements comprising a flexible supporter 22, a concealment shield 28, and two corner support components 23 and 25 that provides support for corners 50 and 52. Wherein internal flexible supporter 22 enabling the body shape enhancing apparatus 1 to cradle and hold with high flexibility, resiliently, engagement, and retractability to wearer's undercarriage and crotch region. The concealment shield 28 for concealing the visibility of the inner components and outline of the genitals of a wearer of the body shape enhancing apparatus 1 through the wearer's clothes while also conforming to the shape of the wearer's undercarriage such that the concealment shield 28, body shape enhancing apparatus 1, or its internal components are not visible through the wearer's clothes. The two corner support components 23 and 25, support and may fill the top front corners 50 and 52 of the pelvic front section 2 to create a seamless and invisible appearance underneath the clothing of a wearer of the body shape enhancing apparatus 1 and may aid in creating a thigh brow and or upper thigh groin crease and/or hip crease.

In one or more embodiments of the present disclosure, body shape enhancing apparatus in an embodiment with or without detachable or attached lateral fastener, may be made as follows, however not limited to this examples configuration, order, and may include less or more components and or parts. The top surface 40 of outer casing 3a and bottom surface of outer casing 3b extends to rear outer shell casing 3c. that, after assembly is continuous with top surface 40 and bottom 42 respectfully.

The outer edges of both the top 3a and the bottom 3b outer shell casings are lined up on top of each other, which the top outer casing 3a and bottom outer casing 3b are then partially attached to each other, about halfway or so from a front section 2 to about the middle section 4 of the outer shell casings. Rear outer casing 3c is left unattached until internal components are inserted. Top outer casing 3a and bottom outer casing 3b may be attached by sewing, bonding, seamless circular knitting, special or customized stitching and or machinery, sealing or any attachment or linking means known in the art. The preferred method of attachment results in a seamless finish and/or structure results in a seamless undetectable finish and/or structure underneath the wearers undergarment, garment, or combination thereof. The top 3a and bottom 3b outer casings may first be partially attached or sewn together from front section 2 through middle section 4, about one-half the length of the outer shell casing, while from middle to the rear outer casing 3c unattached to allow for the insertion of internal components such as concealment shield 28 may now be inserted between the partially attached outer casings 3a and 3b and may be secured to the internal wall of the bottom outer casing 3b of front section 2 via a self-adhesive means embedded on it, or other means known in the art. Concealment shield 28 (whose preferred location is shown in simplified form in dashed lines in FIG. 3 and whose example structure is shown by way of example in FIG. 9.

Next, corner support components 23 and 25 may inserted, positioned and can be secured by any means known in the art, into the inside of each of the outer corners 50 and 52 of the pelvic front section 2 of outer casing 3 on or about the top center of previously inserted concealment shield 28. Corner support components 23 and 25 support and can fill the top outer corners 50 and 52 of the pelvic front section 2 to create a seamless and invisible appearance underneath the clothing or undergarment of a wearer of the body shape enhancing apparatus 1 and may also aid in creating a thigh brow. Corner support components 23 and 25 may be made of silicone or any other like textiles that are undetectable underneath, lightweight, or a comparable fiber or a combination thereof.

A first internal padding layer 30b may be layered on top of the concealment shield 28 (optional in some embodiments). The flexible supporter 22 may be inserted next on top of internal padding or whatever was last inserted in the outer casing 3, which may be followed by a second internal padding layer 30a, layered on top of the flexible supporter 22. Internal protrusion support member 11 may then be inserted into outer casing 3c of rear section 7 wherein the bottom surface 42 of internal protrusion support member 11 is adjacent to the bottom surface 36 of the bottom rear base section 12. Rear outer casing 3c comprises fabric extending from bottom outer casing 3b, which extends beyond the length of the top outer shell casing 3a when the top outer casing 3a and the bottom outer casing 3b are lined up. This excess fabric is folded, and lifted up and over internal protrusion support member 11, blanketing internal protrusion support member 11, and which is secured by any means known in the art to the top outer shell casing 3a, forming protrusion 10 which takes the shape of the internal protrusion member support member 11.

Internal protrusion support member 11 may comprise of cardboard or any other malleable materials having structural integrity, which may include biodegradable, soft wood, plastic such as Polylactic Acid (PLA), Polybutylene adipate terephthalate (PBAT), Polybutylene Succinate (PBS), Polyhydroxy alkenoates (PHA), graphene and or starch blends. Internal protrusion support member 11 may be of various materials and/or shapes. Internal protrusion support member 11 is configured in a triangle shape in the embodiments shown in the figures, however, it is not limited to any particular shape or size, texture, weight, or material, or style and/or component(s). Internal protrusion support member 11 helps enhance and strengthen and maintain the shape and integrity of protrusion 10 so as to withstand the compression and effects of the insertion in between the wearer's buttocks cheeks, and bodily movement as well as to aid in supporting the lifting, firming and separating of the wearer's buttocks. After internal protrusion support member 11 has been positioned inside the rear section 7, the remaining detached ends of the rear outer casing 3c are then attached and the enclosure is complete for this embodiment. The body shape enhancing apparatus outer shell casing 3 is not limited to a three-section configuration, it can be made with more or less sections, but with a least one section in some embodiments or may be a single continuous outer shell casing instead of a casing that requires attaching multiple sections together.

Figure 9:
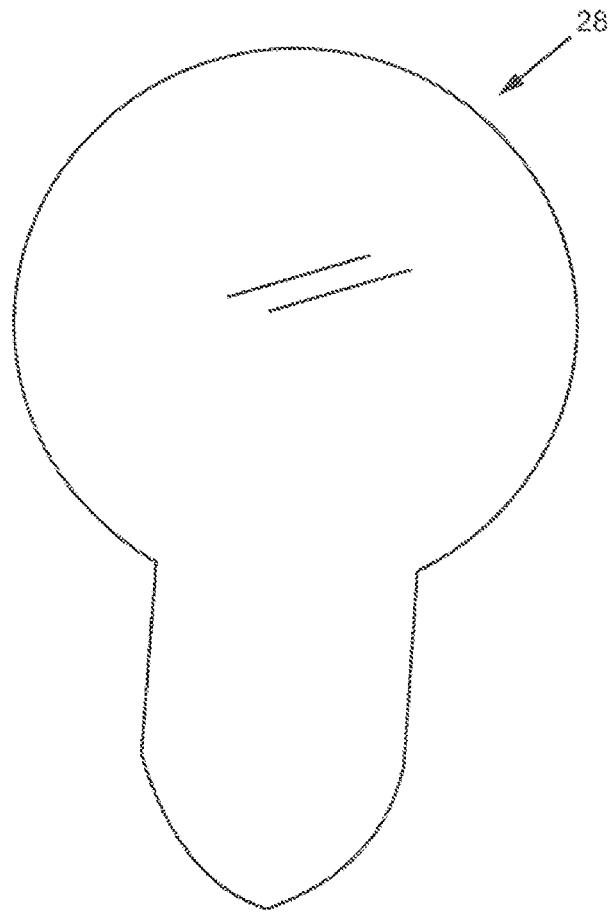
FIG. 9 is a front view of a concealment shield for use within the body shape enhancing apparatus, in accordance with an embodiment the present disclosure.
Figure 10:
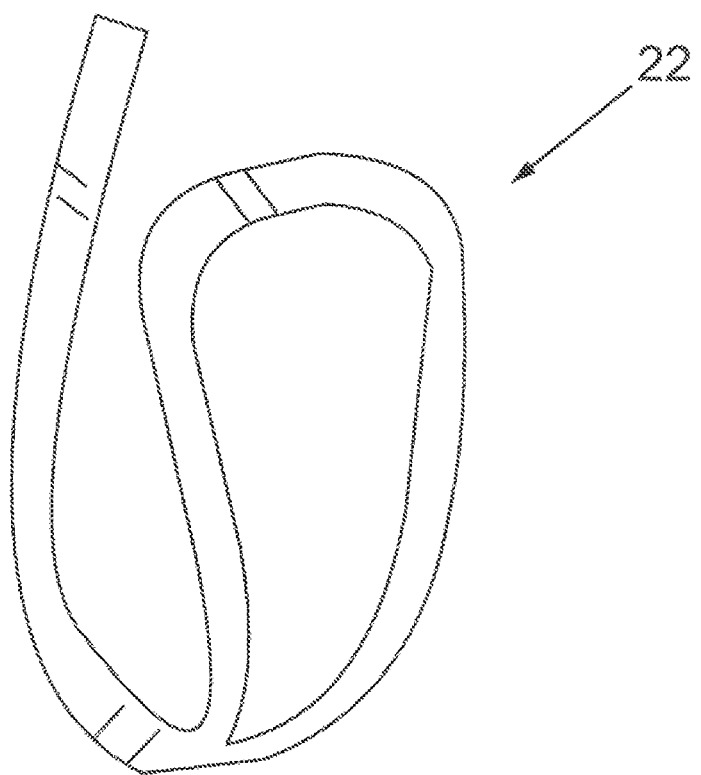
FIG. 10 is a perspective view of a flexible supporter for use within the body shape enhancing apparatus, in accordance with an embodiment the present disclosure.

The concealment shield 28 is shown by way of example in FIG. 3 (whose preferred location is shown in simplified form in dashed lines) and FIG. 9. The concealment shield 28 may be shaped like but not limited to a tear drop with the curved end of the tear drop positioned proximal to the pelvic front section 2 of the body shape enhancing apparatus 1 and the pointed end of the tear drop terminating about the middle section 4 of the body shape enhancing apparatus 1. The concealment shield 28 may be made of silicone or felt, may or may not be slightly padded and with a commercial grade sticky like gel adhesive or double sided tape or any adhesive known in the art, or combination thereof, or similar materials capable of concealing the visibility of the outline of a wearer's genitals, smoothening out and blending in any ridges, bumps, ripples, and or unevenness that may appear through the wearer's clothes while also conforming to the anatomical undercarriage shape of the wearer such that the concealment shield 28 is not visible through the wearer's clothes or through body shape enhancing apparatus 1 outer casing 3 and is positioned on the inside of bottom side layer 3b, facing and adhering to the inside of front sections 2, and middle section 4 of bottom outer casing 3b of body shape enhancing apparatus 1.

In one or more embodiments of the present disclosure internal padding 30a and 30b whose preferred locations are shown in simplified form by dashed lines in FIG. 4 are configured to fit across the pelvic front section 2 and middle section 4 but not limited to of body shape enhancing apparatus 1. Internal padding 30a and 30b and or in an all-fibers embodiment is preferably but not limited to fibers such as fabric, foam Hemp fabric, non-woven, bamboo, organic cotton, viscose, bamboo, cellulose, and or fabrics including Hemp, or possibly bi-component fibers created using polyethylene terephthalate and contains optically active particles and thermal active minerals which can increase the transcutaneous oxygenation to the wearer and a useful fiber be incorporated into the core of body shape enhancing apparatus. RDA feathers may also be an option to use as a padding or filler within the body shape enhancing apparatus or a combination thereof. However, internal padding 30a and 30b may be made of any materials known in the art for providing padding or cushion and may be of optional use, depending on the desired size of the body shape enhancing apparatus 1 and of the wearer. Flexible supporter 22 is a flexible spring like, resilient and highly retractable that serves as a supporting structure made of materials such as retractable plastic, acrylic acetate, metal sheet, flexible wire or any other flexible and retractable materials, and is preferably positioned in the center of the pelvic front section 2 of the elongated body, between internal padding 30a and 30b, and extending through the length of the elongated body to about the middle of the elongated body until at about internal protrusion member 11. The flexible supporter 22 is disposed to induce an effect of a tensioned gripping, hugging and holding engagement between a wearer's pelvis, groin and buttocks when body shape enhancing apparatus 1 is in use, without or with us of an undergarment or garment causing the body shape enhancing apparatus 1 to appropriately cradle the wearer's undercarriage. The flexible supporter 22 comprising a rounded top proximal to a top edge of the pelvic front section 2 and two parallel arms extending from the rounded top and towards the middle section 4 of the body shape enhancing apparatus 1, terminating and or intersecting with a distal end at about the internal protrusion support member 11.

In one or more embodiments of the present disclosure, body shape enhancing apparatus 1 which may incorporate flexible supporter 22 within its internal cavity, which flexible support 22 may provide flexible, self-retaining, retraction ability, engagement, adherence and retainment to the undercarriage of wearer without the use of any supporting straps or strings. Flexible supporter 22 is strategically centered and positioned within the center of the body shape enhancing apparatus 1 and may or may not need to be secured in place. In one or more embodiments of the present discourse, body shape enhancing apparatus 1 is readily adaptable and self-adjustable to the body of the wearer, body shape enhancing apparatus is responsive to body movements and adjusts accordingly while positioned and when in operation respectively whether with or without flexible supporter 22 incorporated internally. In some embodiments flexible supporter 22 may not be included.

FIGS. 11A through 11D illustrate the flow of a method of construction of the body shape enhancing apparatus's outer shell casing 3, wherein FIG. 11A illustrates the top and bottom outer shell casings disassembled. FIG. 11B illustrates the top and bottom outer shell casings lined up for initial partial attachment to each other and in preparation for internal components insertion, if any are to be included. FIG. 11C illustrates the top outer shell casing 3a and bottom outer shell casings 3b lined up for attachment to each other and a back rear outer casing section 3c is folded up. FIG. 11D illustrates the top 3a and bottom 3b rear outer casings 3c lined up for protrusion support member 11 insertion and for remaining attachment of top and bottom of outer shell casings to each other, and a protrusion section folded up, then lifted up and over internal protrusion member 11 after its insertion and back outer casing 3c is prepared for final attachment to the top outer casing 3a.

In one or more embodiments of the present disclosure, body shape enhancing apparatus 1 may be either permanently or removably attached to any undergarment, garment, a custom undergarment 300, or any article of forked fabrication worn on the lower body, such as but not limited to leggings 700 or hosiery 800 for further enhancing the shape of a wearer's lower body. The custom undergarment 300 or any undergarment, shapewear, or any forked lower body garment such as, but not limited to leggings 700 or hosiery 800 may be any length, terminating at about the thighs, or ankles or knees, or calves, or groin of the wearer. Hosiery 800 may or may not be footless.

In one or more embodiments of the present disclosure, body shape enhancing apparatus 1 may be incorporated into hosiery 800, which may be fabricated with advanced compression technologies. The hosiery 800 offers the same body shaping and enhancing features and benefits aforementioned to the wearer as well as may wick sweat and moisture away, is comfortable and not overly constrictive, may provide muscle recovery. The hosiery 800 may be manufactured wherein at least the waistband 354 and legs are each composed of single yarn and a high level and quality of denier known in the art, such as but not limited to spandex. A second yarn may correspond to a textured nylon and maybe in combination with other yarns for the waistband and or body and or combination thereof, with body shape enhancing apparatus respectively incorporated and or embedded within this optional hosiery 800 incorporation.

Figure 16:
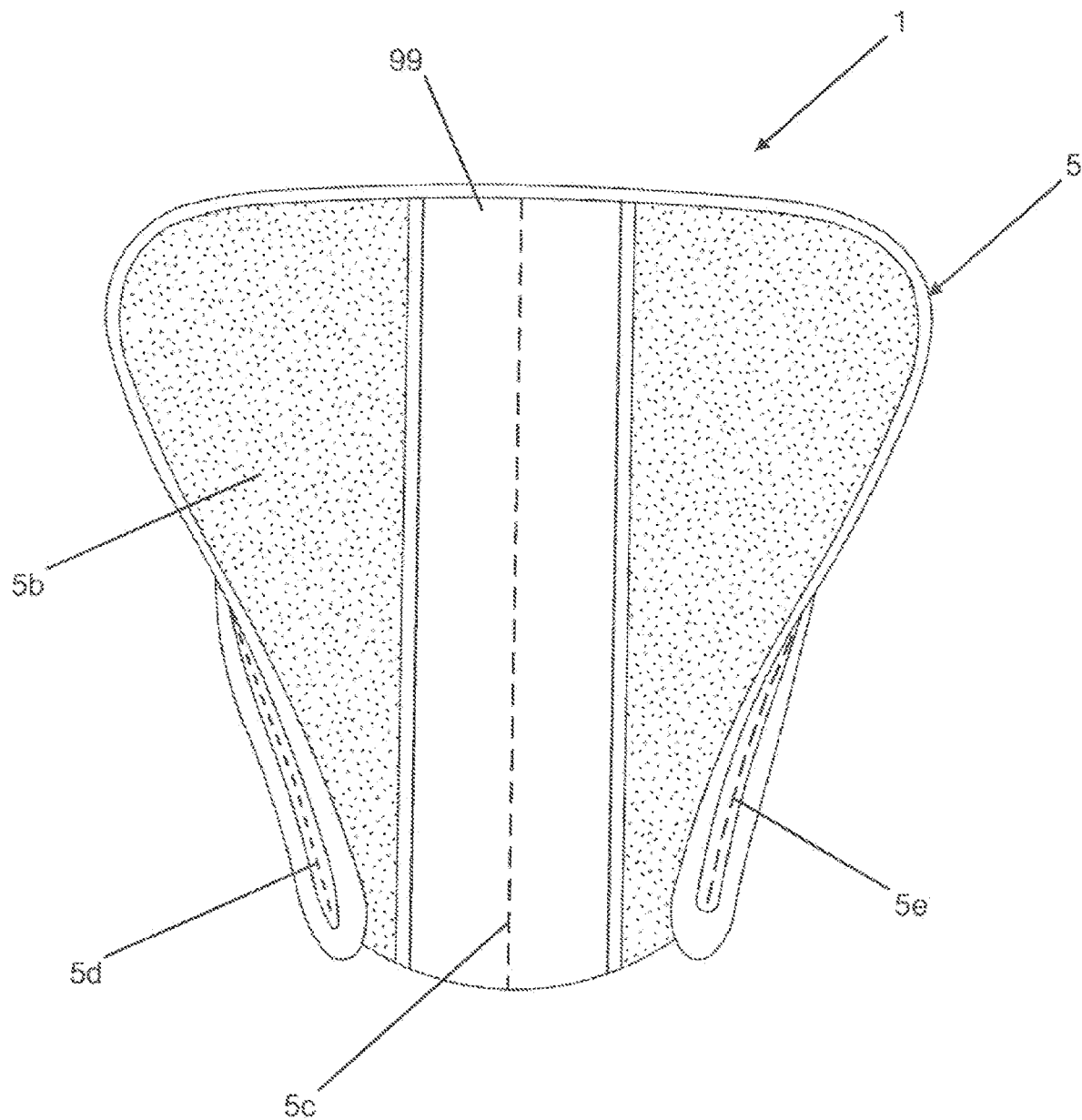
FIG. 16 is a front elevational view of body shape enhancing apparatus with an oversleeve and without lateral fasteners in accordance with embodiments of the present disclosure.
Figure 17:
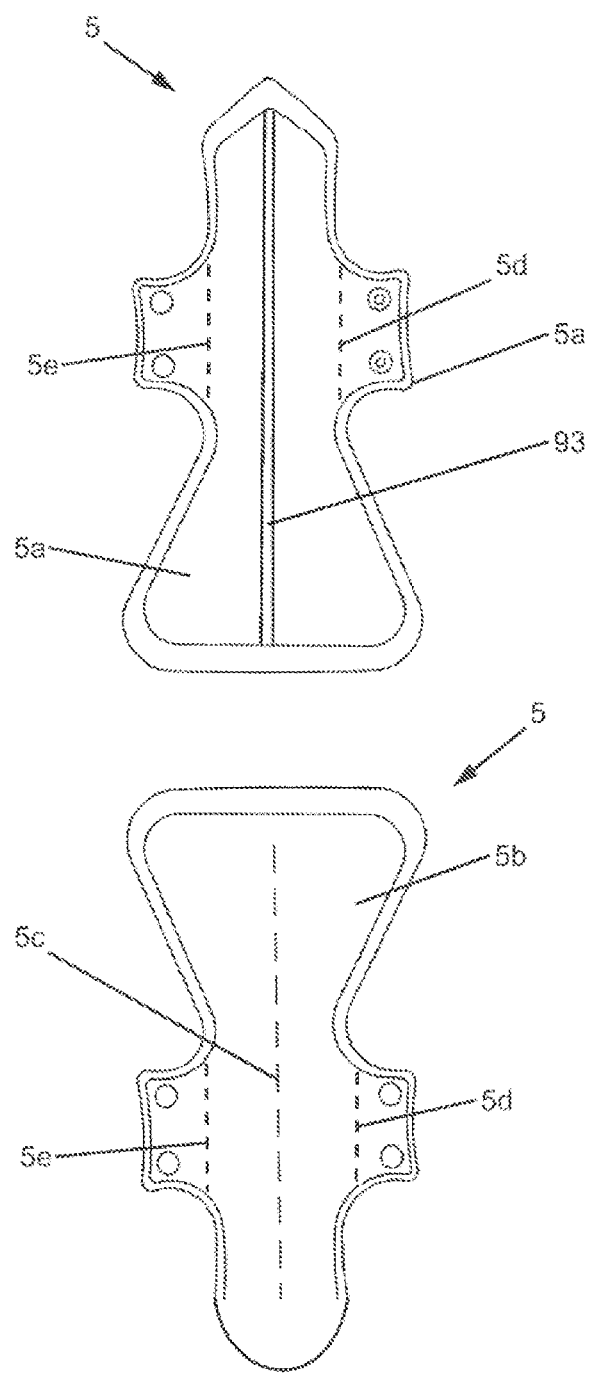
FIG. 17 are elevational views of a top and a bottom of an oversleeve in accordance with embodiments of the present disclosure.

In one or more embodiments of the present disclosure, body shape enhancing apparatus 1 may be attachable to any undergarment, garment, a custom undergarment 300 or a high waisted brief 90 (may include back full back coverage panel 363 in some embodiments, or other style), or any brief or undergarment or garment, or forked lower body garment such as leggings 700 or hosiery 800 but not limited to, by any means, shape, style and or design or available means of adhesion known in the art. In one or more embodiments of the present disclosure, body shape enhancing apparatus 1, by way of example only, shown on FIG. 16 wherein the two vertical centered lines 99 adhesion strips may indicate an example of a location at the bottom of outer casing 5b, but not limited to this location or size, of adhesion strips which will vary, of the means of adhesion which may be dependent on the desired hold and/or effect. The means of adhesion could include double sided tape, silicon grips (on the top or bottom), and or magnet tape (which is also known for stimulating and promoting circulation to the body) or any other attaching or adhesion means known in the art, or a combination thereof.

In one or more embodiments of the present disclosure, body shape enhancing apparatus 1 may be attachable to any undergarment, garment, a custom undergarment 300 or a high waisted brief 90, or any brief or undergarment or garment, or forked lower body garment such as leggings 700 or hosiery 800, but not limited to any style or configuration, and may or may not include a high waistband 354 (anywhere above the belly button, closer to rib cage), or a lower waistband 356 (anywhere below the belly button, closer to pelvis).

Figure 5:
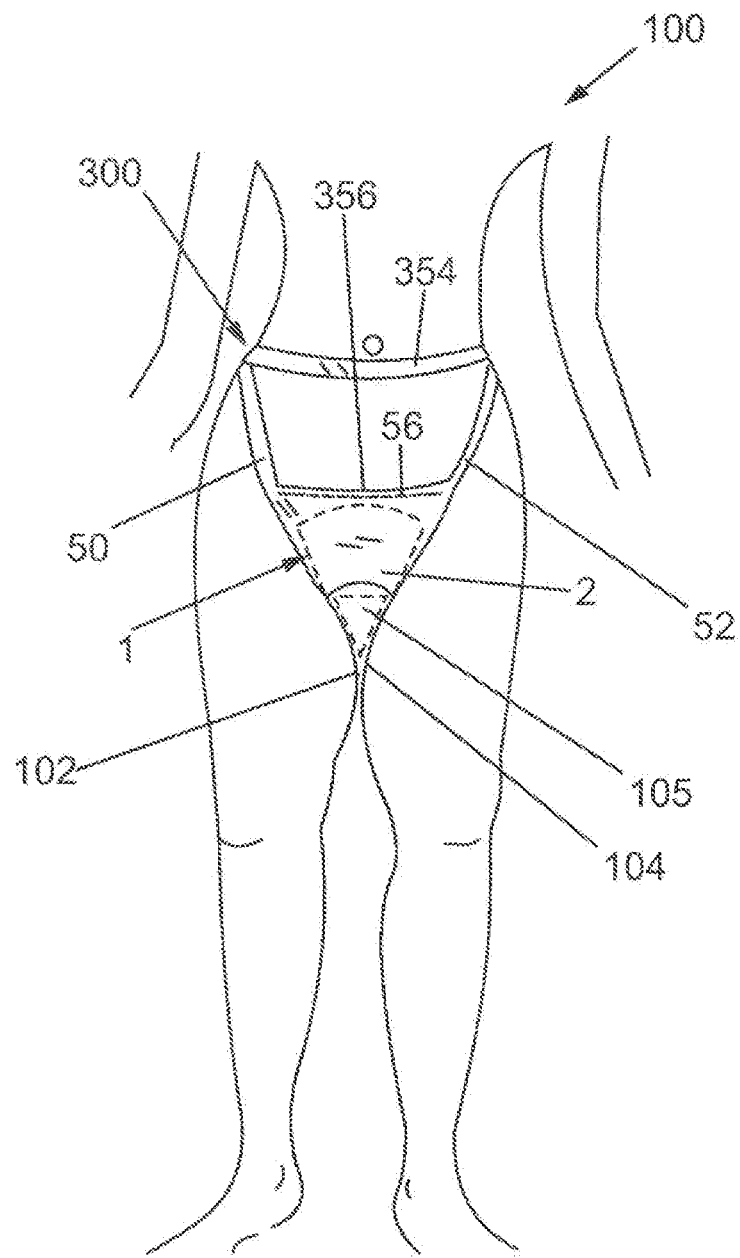
FIG. 5 is a simplified diagram of a front view of part of a female person, with a location to show the placement of the body shape enhancing apparatus, worn in combination with a custom undergarment in accordance with embodiments of the present disclosure.
Figure 12:
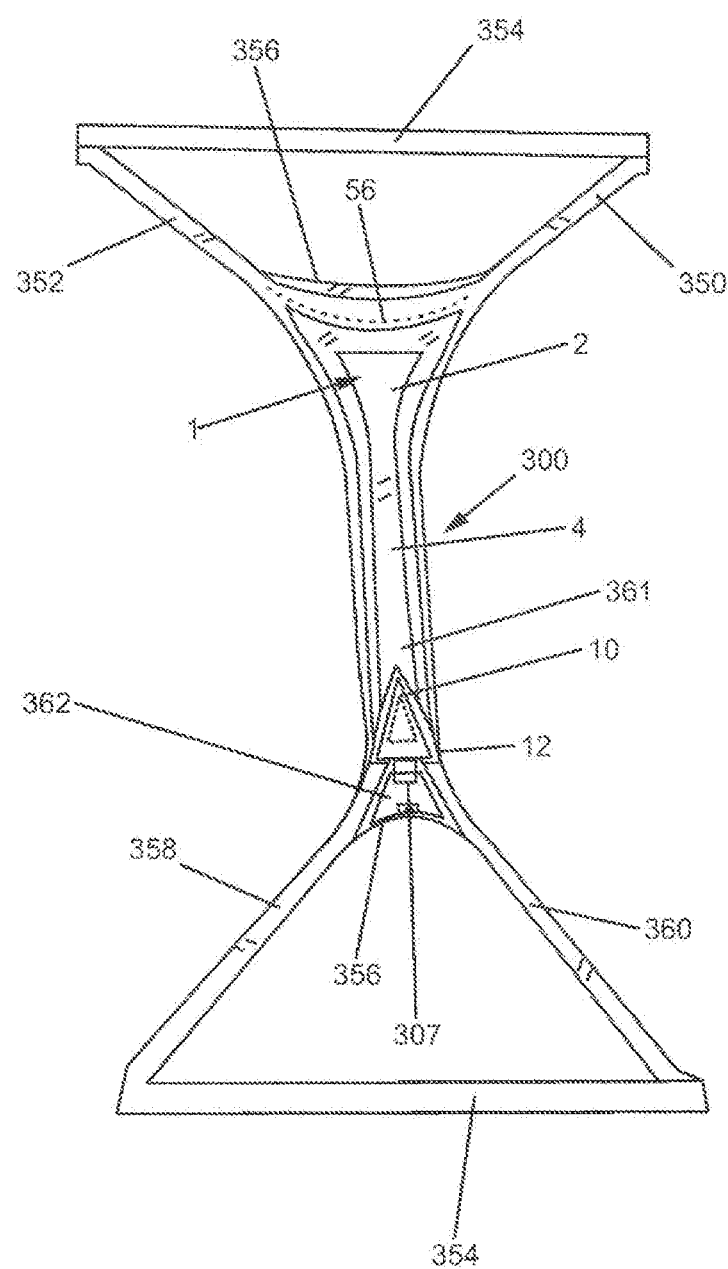
FIG. 12 shows a top simplified view of body shape enhancing apparatus within a custom undergarment, wherein the custom undergarment is in an example thong style in accordance with embodiments of the present disclosure.
Figure 13:
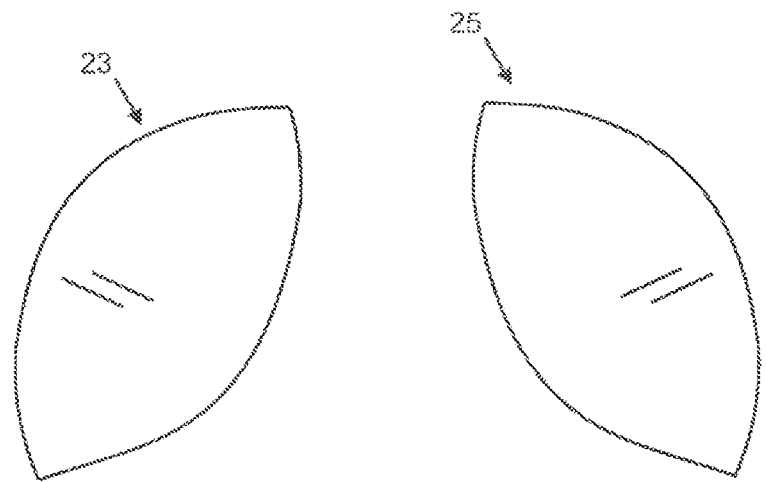
FIG. 13 is a simplified view of corner support components for insertion into body shape enhancing apparatus in accordance with embodiments of the present disclosure.
Figure 14:
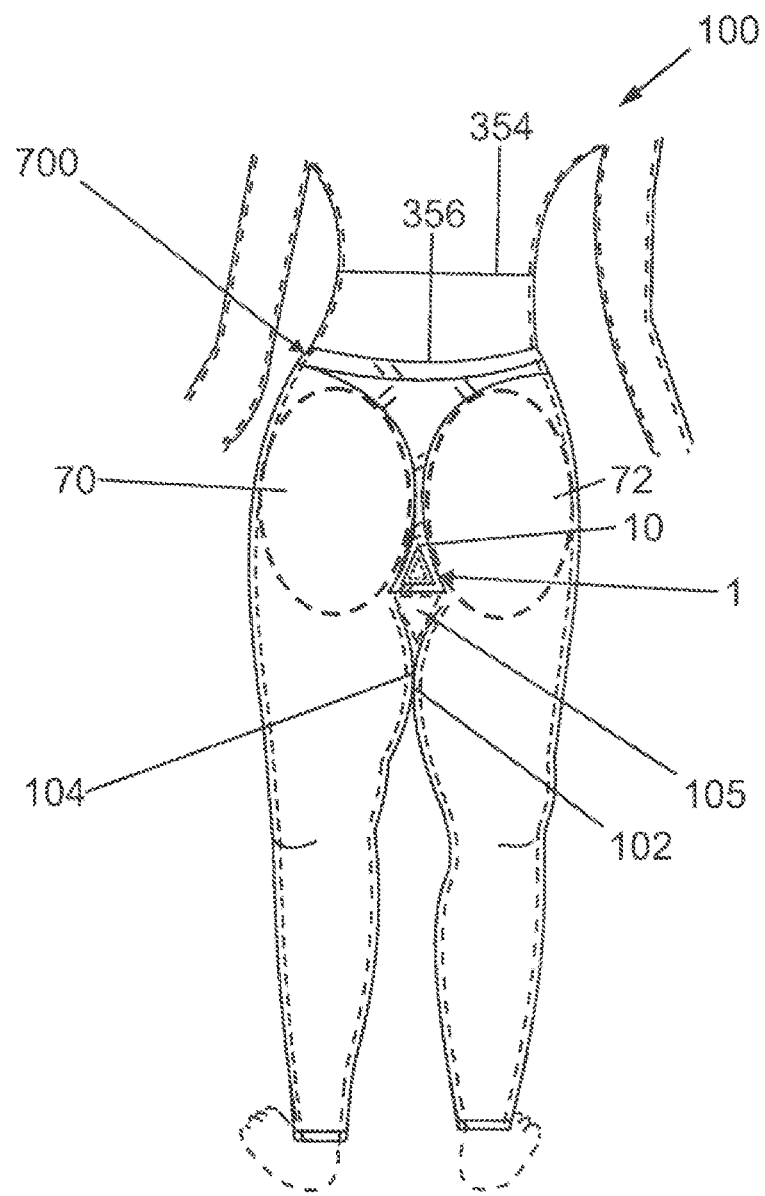
FIG. 14 is a simplified diagram of the rear perspective view of part of the female person wearing leggings that incorporate body shape enhancing apparatus in accordance of embodiments of the present disclosure.
Figure 15:
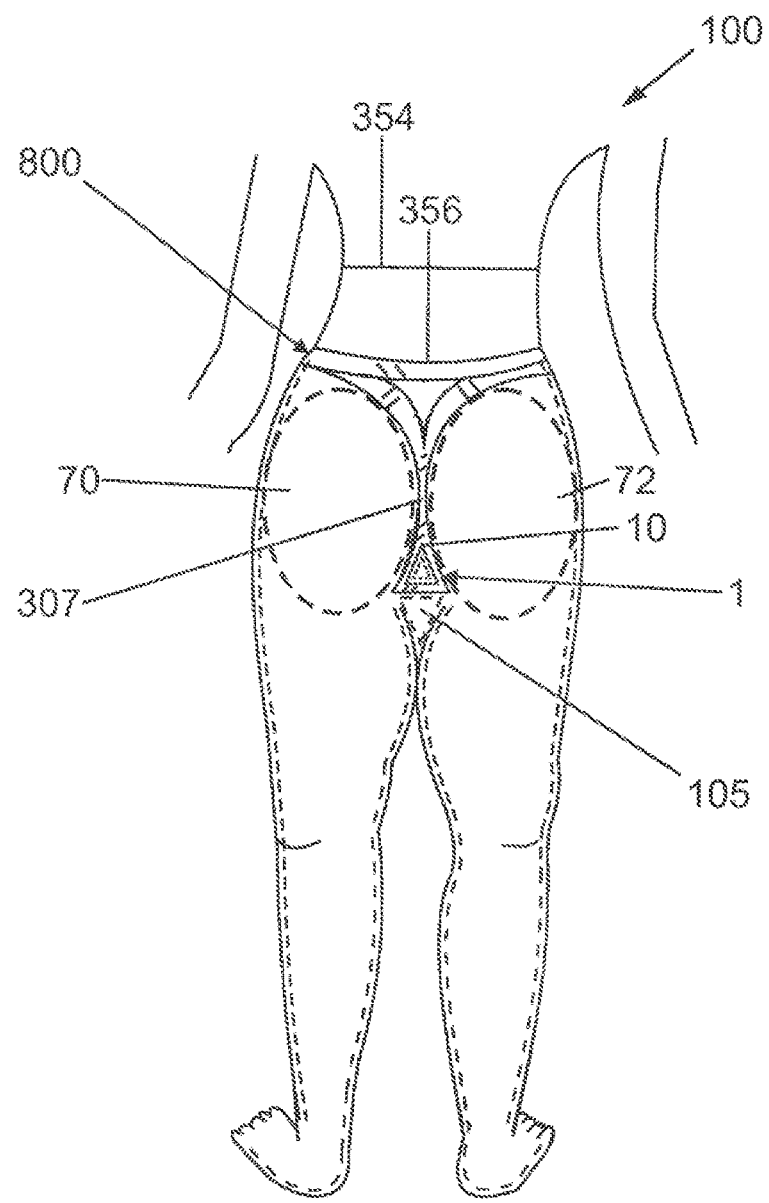
FIG. 15 is a simplified diagram of the rear perspective view of part of the female person wearing hosiery that incorporate body shape enhancing apparatus in accordance of embodiments of the present disclosure.

In one or more embodiments of the present disclosure, body shape enhancing apparatus 1 may be inserted into a custom undergarment 300 or any body shape enhancing coordination garment or undergarment embodiments through a pelvic pocket slit 56 of the custom undergarments 300 as shown by way of example in FIG. 5 and FIG. 12. Once body shape enhancing apparatus 1 is inserted into a custom undergarment 300 it can be slid all the way though a protective pocket 361 which is like a cavity, such as a double-sided gusset, sock compartment, or placed directly on top of the crotch region of the undergarment, using any means of adhesion known in the art, to be positioned at about the crotch region of the undergarment so that body shape enhancing apparatus 1 is aligned with the wearer's undercarriage with pelvic front section 2 about the pelvis, middle section 4 through the undercarriage, and terminating at protrusion 10 about the anus.

In one or more embodiments of the present disclosure, body shape enhancing apparatus 1 is permanently attached to a seamless undergarment that can be worn underneath a garment without negatively affecting the appearance of the wearer or the garment on the wearer. In one or more embodiments of the present disclosure, body shape enhancing apparatus 1 is permanently or removably attached to a brief undergarment 90 which may or may not have a reinforced control top portion having shaping and control characteristics, where the reinforced control top portion may terminate at the top of the waist region of the wearer just under the wearer's bust or lower or midsection torso and or waist and may have a knitted-in welt to provide the wearer with shaping support. The reinforced control top portion may extend down to about the crotch, or thighs, or knees, or calves, or ankles of the undergarment, and at the least far enough to provide support over the abdomen and pelvis, or more.

In one or more embodiments of the present disclosure, shown by way of example in FIG. 1A, protrusion 10 protrudes vertically from the bottom of rear base section 12, however it is extremely crucial that is understood that protrusion 10 is not limited to any shape, size, direction, or protrusion of how or where it is protruding, or not protruding. When body shape enhancing apparatus 1 is in use protrusion 10 is inserted and positioned between a wearer's buttocks cheeks 70 and 72. Body shape enhancing apparatus 1 provides a different type of placement, positioning and structure than was currently offered, and which can deliver body shape enhancements and or improvements such as, but not limited to lifting, separating, firming buttocks, and capable of creating a thigh gap 105 (example shown on person 100 from a frontal view and back view, in FIGS. 5, 6, 7, 8, 14, and 15 in various embodiments of body shape enhancing apparatus) as well as separating the inner thighs 102 and 104 from over lapping, and provides genital protrusion concealment to wearer. Additionally, it may also help with lower body structural reformation and correction by widening, or reforming and or training any of the hip abductor, quadratum lumborum hamstring muscles, groin, hips, femur, and skeletal frame and or combination thereof. It is crucial that it is understood that the thigh gap 105 shape, or size, or space, or gap, and or opening in which body shape enhancing apparatus creates between the wearer's thighs, and or underneath their buttocks, when in operation is not limited to any one specific shape or size and will vary by wearer depending on wearers existing body shape, type and or size. When in operation and positioned with top of front section 2 laying on a wearer's pelvis, pressed against lower pelvic, and configured to touch the wearer's crotch skin and middle section 4 lays at the perineum shaft and cradles the undercarriage to aid in separating the wearers thigh, and when bottom rear base section 12 lays under buttocks and about the anus, with protrusion 10 positioned in between the wearer's buttocks 70 and 72 body shape enhancing apparatus creates a thigh gap or space 105 between the wearer's thighs and or underneath crotch and buttocks of undercarriage.

Figure 6:
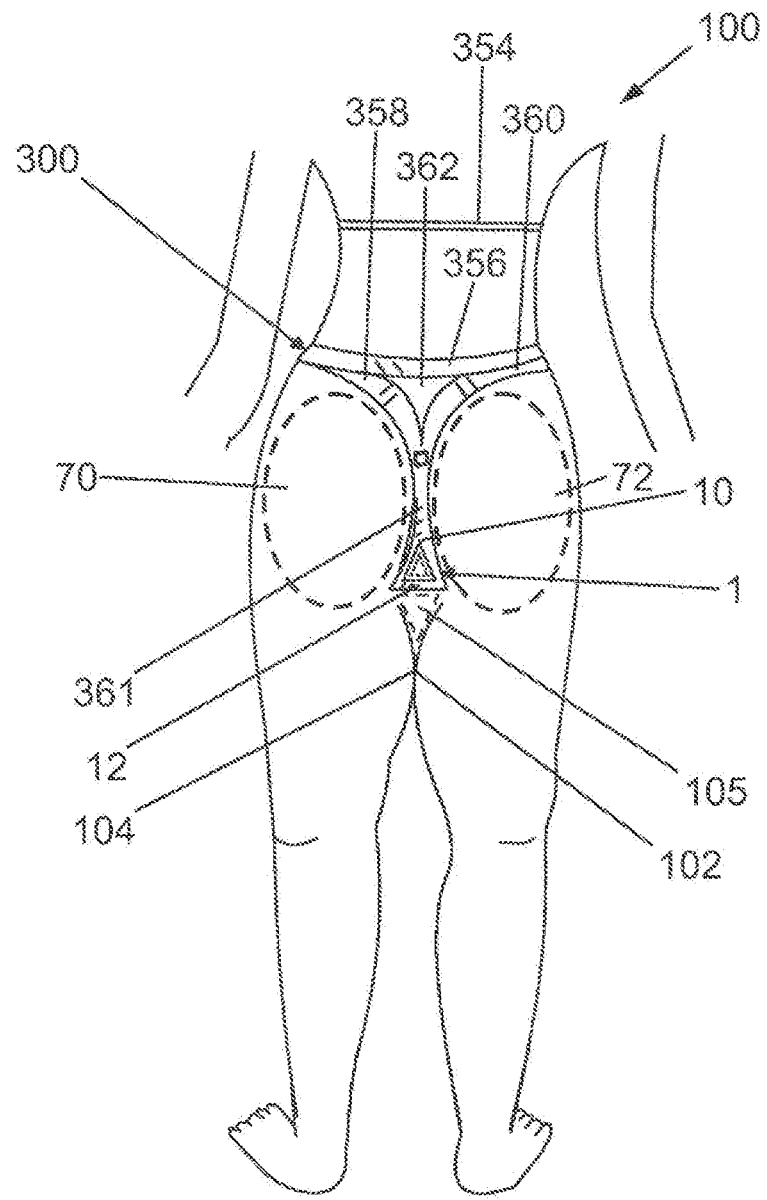
FIG. 6 is a simplified diagram of a rear view of part of a female person, with a location to show the placement of the body shape enhancing apparatus, worn in combination with a custom undergarment in accordance with embodiments of the present disclosure.
Figure 7:
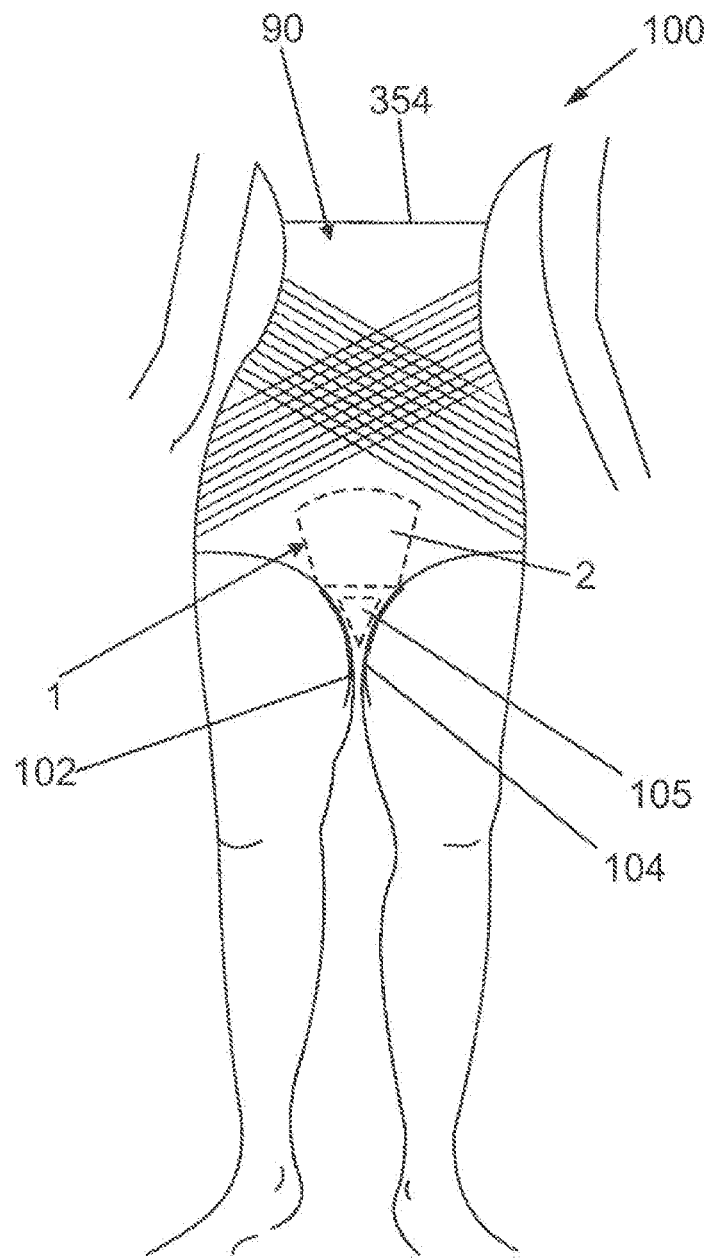
FIG. 7 is a simplified diagram of a front view of part of a female person, with a location to show the placement of the body shape enhancing apparatus, worn in combination with a brief undergarment with control top portion in accordance with embodiments of the present disclosure.
Figure 7B:
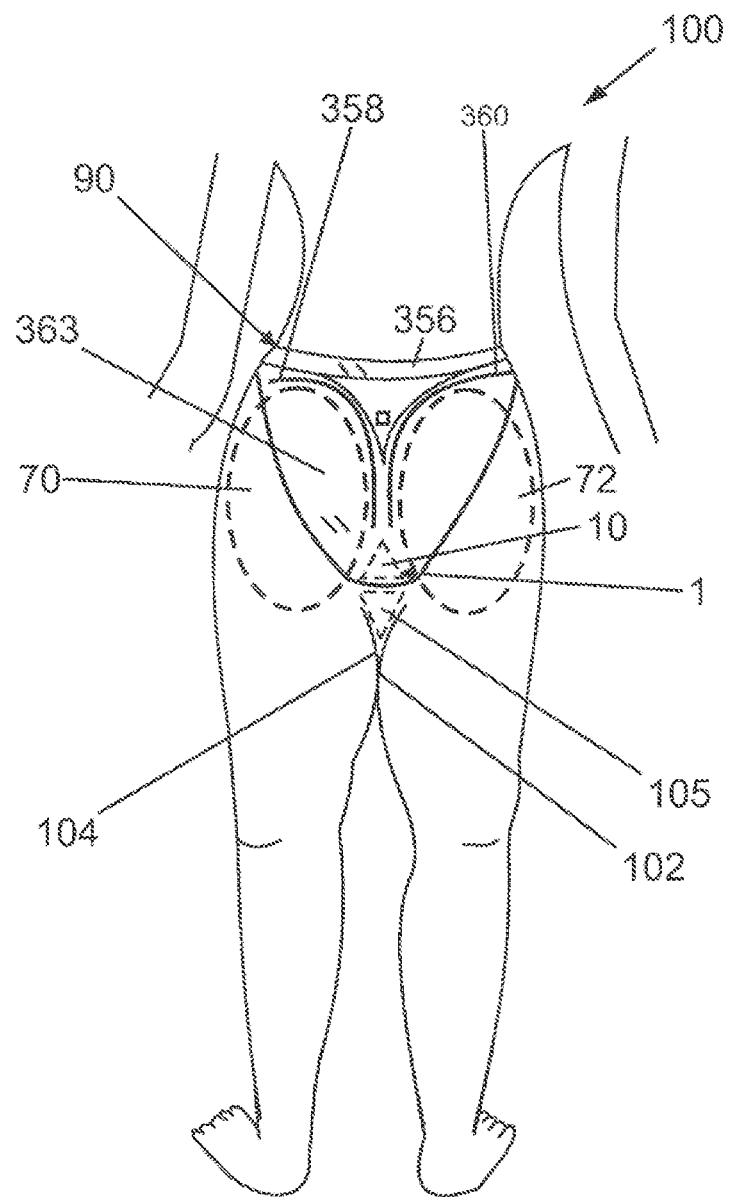
FIG. 7B is a simplified diagram of rear view of part of a female person, with a location to show the placement of the body shape enhancing apparatus, worn in combination with a brief undergarment in accordance with embodiments of the present disclosure.

In one or more embodiments of the present disclosure, Body shape enhancing apparatus is capable of creating a thigh gap, shown by example only on person 100 as 105, in FIGS. 5,6,7, 7B,14, and 15, with the location of body shape enhancing apparatus as 1. The shape which body shape enhancing apparatus 1 creates for thigh gap 105 may or, may not be a triangle, a square or perhaps possibly even a circle or quadrilateral, and will vary by wearer and is not limited to any specific shape or size, and can be any shape or size. The shape and or size of the thigh gap 105 will depend on the natural shape characteristics of the individual wearer. The shape of thigh gap 105, on person 100 in FIG. 5 (form a front view) and FIG. 6 (from a rear view), is only an example of it shown as triangular and should not be limited to any shape or size. Thigh gap 105 may be identical from both the front and rear of the wearer or person 100 or may vary from the front to the back. However, protrusion 10 of the apparatus 1 is to be worn in the back of the wearer, by inserting it between buttock cheeks 70 and 72 as shown in FIG. 6 of person 100, with the front, section 2 of the body shape enhancing apparatus 1 to be worn with front section 2 at the pelvic and under the entire vulva extending with middle section 4 under the perineum shaft, and rear base section 12 section under buttocks, and protrusion 10 positioned between the wearers buttocks cheeks 70 and 72. Examples are shown on in FIGS. 5,7,7B,14, and 15 on person 100.

In one or more embodiments of the present disclosure, body shape enhancing apparatus 1 is made primarily of disposable and/or recyclable materials that are capable of readily absorbing liquids. In one or more embodiments these embodiments, body shape enhancing apparatus 1 may be used as a body shape enhancing sanitary napkin providing a wearer with body shape enhancing benefits on days wearers may be on their menstrual cycle. In these embodiments, body shape enhancing apparatus 1 may be with or without lateral fasteners 6 and 8. Said lateral fasteners 6 and 8 may be in the form of lateral extensions (or wing-like structures) which may have means of adhesion on their undersides to assist in providing stability when these embodiments of body shape enhancing apparatus 1 are in use. In some embodiments of the present invention there exist one or more lateral fasteners 6 and 8 extending from at least one side edge of the body shape enhancing apparatus 1. The means of adhesion on the lateral fasteners 6 and 8 allow a wearer to attach these embodiments of body shape enhancing apparatus 1 to a wearer's garment or undergarment. In one or more embodiments of the present disclosure that comprises lateral fasteners 6 and 8, the lateral fasteners 6 and 8 may be detachable from body shape enhancing apparatus 1 through any means known in the art, which may include perforations. Embodiments may also include antimicrobial, and hypoallergenic properties and/or skin or fiber protectants.

In one or more embodiments of the present disclosure, there may be a coating that is antibacterial, antimicrobial, antifouling or anti odor preventative or protective, hypoallergenic, or any combination thereof, applied to and/or impregnated into the top outer shell casing 3a and the rear outer casing 3c, which covers and encloses internal protrusion support member 11 and becomes protrusion 10, a. In one or more embodiments of the present disclosure comprising lateral fasteners 6 and 8, said coating may also be applied to and/or impregnated into the top surfaces of the lateral fasteners 6 and 8. In one or more embodiments of the present disclosure, there exists another alternative protective covering in the form of an apparatus liner that may be removably attached to the top outer casing 3a, by any adhesion means known in the art. Apparatus liner can serve to provide protection from bodily fluid release, may be disposable, light weight and skin friendly.

Figure 18:
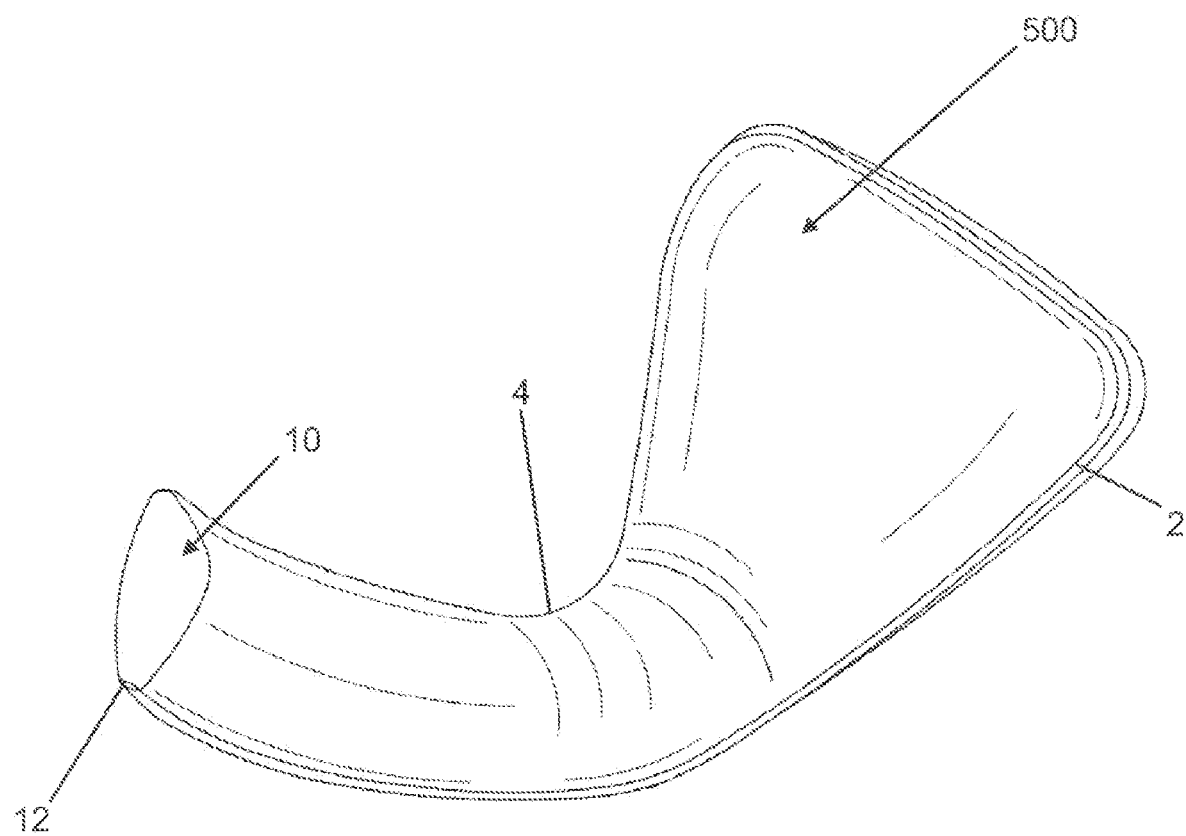
FIG. 18 shows a perspective view of another embodiment which is comprised primarily of fibers of the apparatus in accordance with another embodiment of the present disclosure.

In one or more embodiments of the present disclosure, body shape enhancing apparatus 1 may be an elongated body shape, or cylindrical 500 (example shown on FIG. 18 of cylinder shaped apparatus 1), or any other shape which may be inserted into a reusable or disposable oversleeve 5, or into alternative embodiments, such as but not limited to accompanying or collaborating ancillary embodiments, undergarments, and or garments. As shown by way of example in FIG. 16 to protect the body shape enhancing apparatus 1 from bodily fluid excretion and provide greater hygienic benefits to the wearer. The adhesion means of body shape enhancing apparatus 1 may be accessible through oversleeve 5, through slits 5c or other openings in the bottom 5b of the oversleeve 5. The oversleeve 5 may use elastic banding, or stretchable elastic or any other fastener or adhesion means known in the art to removably secure itself to body shape enhancing apparatus 1. In embodiments of the present disclosure the oversleeve 5 may have side openings 5e and 5d allowing the lateral fasteners 6 and 8, if they exist on such embodiments, to be accessed by a wearer through the oversleeve 5. The oversleeve 5 may comprise of one unit or may be multiple separate sections requiring fastening after insertion of the body shape enhancing apparatus 1 or may not. Oversleeve 5 may be disposable and or reusable, may or may not include adhesion strips 93 to aid in adhering to skin, on the top of oversleeve 5a of oversleeve 5, to adhere to skin and may or may not be impregnated or coated with the aforementioned coating agents, such as antimicrobial, antifouling, anti-odor agents to protect the oversleeve 5 and or body shape enhancing apparatus 1, as well as keep the wearer feeling and or smelling refreshed, with the option to frequently change, and or dispose of oversleeve 5, when it may become wet from bodily fluid excretion, or any other type of discharge.

Figure 8:
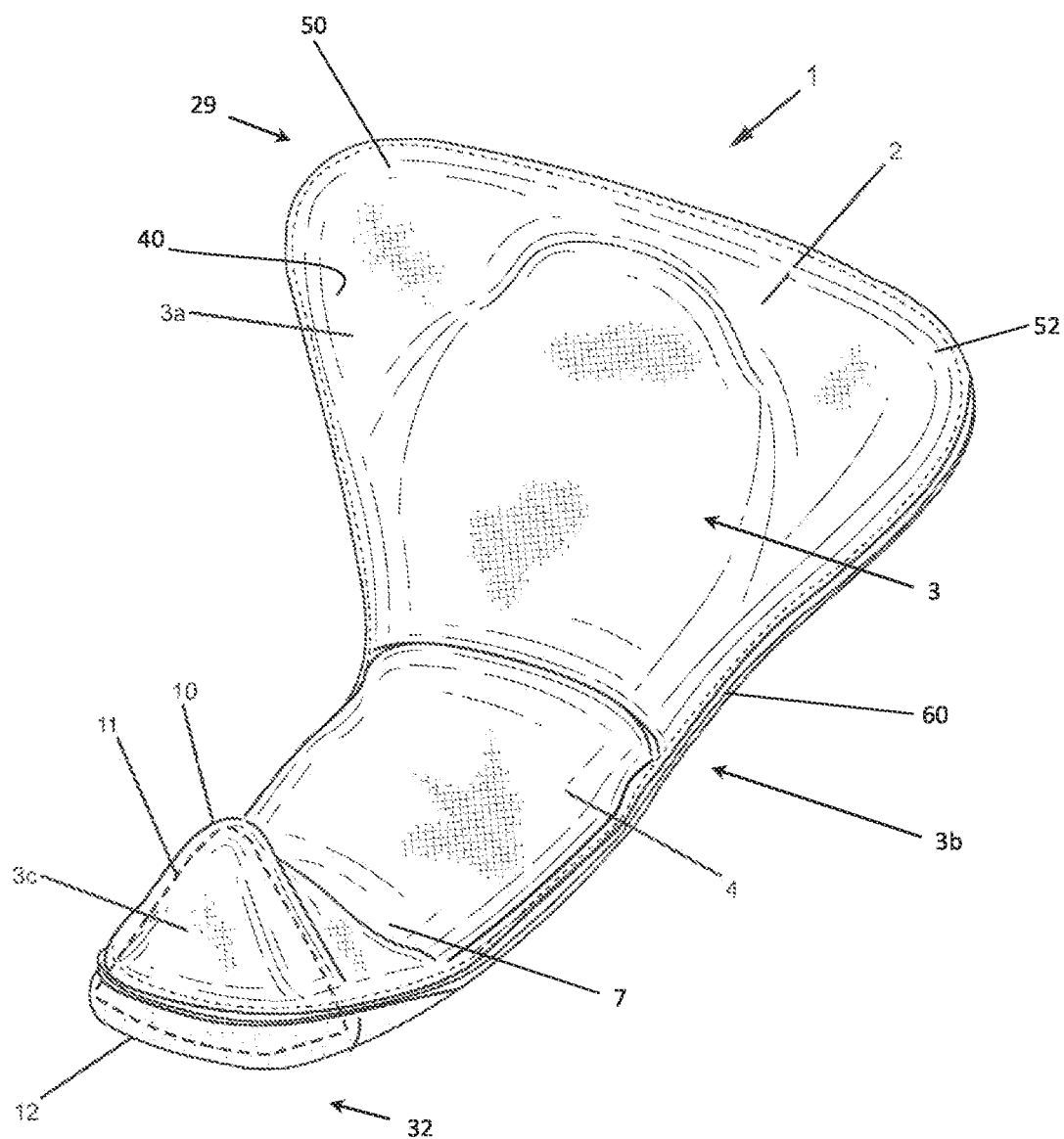
FIG. 8 is a top, left and rear perspective view of a body shape enhancing apparatus without lateral fasteners, in accordance with an embodiment of the present disclosure.

In one or more embodiments of the present disclosure, FIG. 8 shows an embodiment of the present disclosure, without lateral fasteners 6 and 8. In embodiments of the present disclosure, body shape enhancing apparatus 1 may be comprised of absorbent material, for example, cotton, synthetic fibers, polymer-based materials, polyester, rayon, cellulose, viscose, foam, or a blend of materials. The materials chosen may allow body shape enhancing apparatus 1 to be flushable and intended as a single-use disposable product and may or may not include internal components.

In one or more embodiments of the present disclosure, body shape enhancing apparatus 1 may comprise entirely of a moldable material or combination of materials, self-forming to the wearer's shape. In one or more embodiments a preferred embodiment of the present disclosure, body shape enhancing apparatus 1 is a concave structure, cradling to a wearer's undercarriage, however, in one or more embodiments of the present disclosure body shape enhancing apparatus 1 is a convex structure where the sides of body shape enhancing apparatus 1 may curve outward and down towards the wearer's thighs. The suitability of a concave or convex embodiment to a specific wearer of body shape enhancing apparatus 1 may be based on the wearer's lower body shape, size and what shaping benefits the wearer desires to achieve. In embodiments of the present disclosure, body shape enhancing apparatus 1 may be a combination of a convex and concave structure and or shape and or a combination therein.

In one or more embodiments of the present disclosure, body shape enhancing apparatus 1 may comprise entirely of materials that are moldable, primarily silicone, or fiber with give (stretchability) and or self-forming to the wearer's unique, individual shape, body type and/or be comprising of skin friendly or hypoallergenic textiles, cushion, foam padding, silicones or combination thereof.

In one or more embodiments of the present disclosure, the pelvic front section 2 of body shape enhancing apparatus 1 may be of various sizes or thickness and or shapes, such as rectangular, trapezoidal, square, rounded, triangular or any other shape, but not limited to any specific shape or size. As seen in FIGS. 2 and 3 in one or more embodiments of the present disclosure that include lateral fasteners 6 and 8, the lateral fasteners 6 and 8 may further comprise fastener elements 14, 15, 16, 17, 18, 19, 20, 21 for securing lateral fastener section 6 to lateral fastener section 8 or for securing lateral sections 6 and 8 to a wearer's garment or undergarment. Fastener elements 14, 15, 16, 17, 18, 19, 20 and 21 may be hook and loop, snaps, strings, ties, buttons, magnets, sleeves, wings, side clips (like bendable nose guard aluminum used on surgical face masks) and loop, or double-sided adhesive tape or any alternative fastener, or means know in the art for attaching and securing, and or attaching and securing the body shape enhancing apparatus 1 in place.

In one or more embodiments of the present disclosure, as shown by way of example in FIG. 12, the body shape enhancing apparatus 1 is incorporated into a custom undergarment 300. In FIG. 12, an example of the custom undergarment 300, which in this example is a thong style undergarment, includes a double-sided crotch, shown as protective pocket 361, example shown on FIG. 12, which is an inner chamber that secures, protects and positions body shape enhancing apparatus, one or more coordinating straps 350, 352, 358, 360 and 362 and or lifting sling 307. The custom undergarment 300 may have a waistband 354 that sits high on a wearer's body at about the belly button, or higher or may have a lower rise waistband 356 sitting lower on the abdomen, closer to the start of a wearer's pubic hair line. Pelvic pocket slit 56 (an example shown in FIG. 5) serves as the opening that the body shape enhancing apparatus 1 can be inserted into and then pushed through the protective pocket 361. Waist band 354 or hip bands 350, 352, 358, 360 may lay on the upper, higher or lower sides of the hips of person 100, wearer.

In one or more embodiments of the present disclosure, body shape enhancing apparatus 1 lifting sling 307, may also be incorporated into leggings 700 or hosiery 800 but not limited to, provides additional hoisting benefits to wearer when used in coordination and or connection with waistband 354 to lift and pull up the undercarriage of a wearer up to the level desired. further assisting with creation of a larger thigh gap. The wearer will have the ability to adjust the lifting level, by an adjustable means known in the art, such as a strap slider adjustment means. In at least one embodiment the body shape enhancing apparatus may include a adjustable lifting sling 307, known in the art, such as but not limited to a strap slider adjustment means. Furthermore, custom undergarment 300, may be manufactured in a conventional manner with conventional knitted fabric, such as, nylon, LYCRA®, spandex, polyester, silk, cotton, a combination thereof or any preferred seamless fiber or textile known in the art, or a combination thereof. The custom undergarment 300 and or hosiery may be manufactured on a circular hosiery knitting machine using a circular hosiery knitting process to attain seamlessness' in parts or in its entirety or using a Tricot knitting machine with wrap yarns and compound needles with a gauge between 7 and 32, or combination of depending on the needs of different parts in some embodiments, alterative knitting machines known in the art may also be used. A seamless garment or undergarment reduces potential discomfort, conceals the appearance of bulges, and their visibility, and can also provide satisfactory and comfortable hold under clothes. Seamless undergarments smooth out body and are comforting on the skin. Termination points that are comprising of seamless knitting and fabric often help minimize bulges. Body shape enhancing apparatus 1 custom undergarment 300, hosiery 800, leggings 700, or any alternative coordinating, accompanying garments, or undergarments may include circular knitting fabrication or alike.

As stated above, in more or more embodiments of the present disclosure custom undergarment 300 rather than using elastic bands, knitted-in welts are knitted in during the knitting process at the waist-terminating region and at the groin or leg terminating regions. This enables the garment to be manufactured in one continuous knitting process as opposed to performing an additional manufacturing process after the knitting process has been performed in order to attach elastic bands for a more seamless, comfortable and smooth appearance. Circular knitting machines and processes are well known. Those skilled in the art will understand the manner in which the custom undergarment 300 or any alternative embodiments of body shape enhancing apparatus 1 or which body shape enhancing apparatus 1 may be in combination with or may be manufactured within, uses such a machine and process or other known processes in the art.

In one or more embodiments of the present disclosure, body shape enhancing apparatus 1 may be inflatable. In these and other embodiments of the present disclosure, the outer casings 3a, 3b and 3c comprise of a special exterior fabrication that is compatible with the inflatable embodiment, and maybe removeable. Hotmelt welding technology maybe used to configure these embodiments. In one or more embodiments of the present disclosure, body shape enhancing apparatus 1 may be without any internal structural components.

In one or more embodiments of the present disclosure, body shape enhancing apparatus 1 may incorporate electronic textiles, which may include technology for tracking certain metrics of the wearer for example, weight, fat burned, calories consumed, sleep quality, stress level, temperature, electrocardiogramar steps walked through the use of smart technology such as a pedometer or accelerometer. These types of technologies are preferably implemented through embedded sensors in or on the surfaces of body shape apparatus 1 which has direct contact with the wearer's skin. Said technology may be configured to share the tracked data with other devices such as mobile devices, tablets, or desktop computers through the use of a wireless and or Bluetooth or satellite communications network such as Bluetooth or the internet. This sharing capability may allow wearers or third parties such as healthcare professionals to receive alerts if an individual has abnormal deviations in their metrics. Many believe that advances like these can increase compliance and lead to better healthcare outcomes. Smart technology is often incorporated into undergarments, and garment, making body shape enhancing apparatus 1 a good fit for Smart garment or Smart apparatus embodiment. Smart garment technology can be useful with such thigs as monitoring, diagnosing or assessing patterns in health such as temperature, provide wake up alerts, include built-in fatigue monitoring, muscle recovery, connect to smart home systems, to do things like change the thermostat when your body is cold (or hot); Measure vitals health, safety monitoring tracking your heart rate, body temperature, remind you when to take your insulin, when your oxygenation is low and need to grab a glass of water; Track fitness progress, stimulate and oxygenate the wearer with magnetic impulses. Track how many steps the wearer walked today and how many calories the wearer burned while doing so; Provide emergency alert to get help instantly; and more.

In one or more embodiments of the present disclosure, in a preferred embodiment of the body shape enhancing apparatus 1 may also include a seamless closure (not sewn with thread, or sewn with a blind stich sewing method, seamless knitting stich), stitching's in a special undetectable hem, or seam may be used. A waterproof glue or hotmelt bonding may be used to achieve this seamless closure, improving the air permeability and comfort of the body shape enhancing apparatus 1. Seamless closure makes materials more comfortable, lightweight and undetectable.

In one or more embodiments of the present disclosure, body shape enhancing apparatus 1 may include only middle section 4 and protrusion 10, and bottom rear section 12. In one or more embodiments of the present disclosure, body shape enhancing apparatus 1 may include only the pelvic front section 2 and middle section 4 and depending on the desired features and benefits desired. There will be many alternatives, variations and configuration which will be apparent by someone skilled in the art.

In one or more embodiments of the present disclosure, body shape enhancing apparatus 1 may be incorporated and/or embedded into any crotch area of any garment, lower body, undergarment or garment or any forked any garment, such as but not limited to leggings, jeans, pants, jumpsuits, activewear, shapewear, or any lower body wearable. It is understood that body shape enhancing apparatus 1 can be of different configurations and may be used with or without customized articles of attire. It is understood that a person with ordinary skill in the art can select varying embodiments to further the performance, features, benefits and to also provide customization and meet the preferences of the wearer. Body shape enhancing apparatus 1 may be available in several sizes to accommodate a variety of different sizes, body shapes, genders, body weights, and types of wearers. There may be at least one size available but there may be multiple sizes, such as but not limited to X-small, Small, Medium, Large, X-Large, XX-Large, and/or buttocks boost level "1", "2", "3", "4", 5 or "6" wherein "boost level" may be the degree of the thigh gap or space, or opening 105 and or the level of undercarriage and or buttocks lifting the wearer would like to achieve. It is understood that there may be several configurations, combinations, and options to choose from. Customization will be available for body shape enhancing apparatus 1 and its various configurations, embodiments, ancillaries, coordinating articles of fabrication, undergarments, garments, and or combination thereof.

In one or more embodiments of the present disclosure the outer and/or inner composition of body shape enhancing apparatus 1 may be coated with or include therapeutic essentials oils that may aid wearers with sensitive skin and may provide a soothing, therapeutic, and tranquil feeling of comfort as well avoidance of potential allergens, or fabric fouling and/or odor.

In one or more embodiments of the present disclosure the outer and/or inner composition of body shape enhancing apparatus 1 may be coated or permanently infused with silver into the surface of fibers to inhibit the growth of bacteria that may grow or live on fabric therefore eliminating odor causing elements during the life of the undergarment or garment. The undergarment or garment maintains its freshness longer even after multiple washings. And may include aromatics, essential oils, CBD oils, or a combination thereof that may aid wearers scent and comfort, aid with odor and/or fouling smells from perspiration or other bodily fluid release or containment the fibers may be exposed to and may help offset such undesired and embarrassing fibers fouling.

In one or more embodiments of the present disclosure the composition of the outer casings 3a, 3b, 3c, the undergarments, garments, oversleeves, apparatus liner, or a combination thereof, may be of Hemp fabric or a combination of fabrics including Hemp. Hemp is an extremely durable and versatile fabric that uses 50% less water as compared to cotton.

The level of lift that body shape enhancing apparatus 1 may provide, in accordance with one or more embodiments of the present disclosure, may be dependent upon what body shape enhancing apparatus 1 may be attached to. In embodiments of the present disclosure, body shape enhancing apparatus 1 is in combination with a customized undergarment, leggings, or hosiery, and may provide greater lifting capabilities to wearer's undercarriage, as well as creating a thigh gap when in use and the garment or undergarment is hosted all the way up and over the wearer's hip bones. The preferred fibers used in the composition of body shape enhancing apparatus 1, including and combined garments and undergarments, is fit forgiving, comfortable, provides the perfect amount and comfortable hold, without resulting in bulges, or constricting the body of the wearer. Body shape enhancing apparatus 1 can be incorporated or combined or be attached or embedded into any undergarment, swim wear, adult diaper, compression garments, feminine hygiene product, over the shoulder or over the neck attire or product of manufacture. Body shape enhancing apparatus 1 may also exist and operate respectively on its own, with or without any undergarment, garments, or with or without any internal parts.

If body shape enhancing apparatus 1 is attached to a tummy control top, body shape enhancing apparatus 1 may have the benefits of the tummy control or reinforced top as well as the body shape enhancing apparatus 1 benefits of lifting, firming, creating a thigh space, vaginal protrusion concealment, and overall body shaping and enhancing benefits. This rule may apply to all articles that body shape enhancing apparatus 1 is attached or inserted into, worn under or with, or manufactured with.

In one or more embodiments of the present disclosure, body shape enhancing apparatus 1 when in operation and through its strategic placement, structure (anatomically designed to fit and engage with wearer), and design provides a restructuring benefit which can help to correct or improve overlapping or touching thighs instantly, as well as over the long-term use of body shape enhancing apparatus 1. In one or more embodiments of the present disclosure, body shape enhancing apparatus 1 also provides shaping, structural reformation, of wearer's undercarriage by inserting protrusion 10 between the buttocks cheeks of the wearer lifting and separating the buttocks and thighs which causes the inner groin muscles to widen, and reforms, strengthens, and trains the wearer's lower body muscles and skeletal frame. When the body shape enhancing apparatus 1 is incorporated between the wears buttocks cheeks, groin, and legs, force from the body shape enhancing apparatus placement, structure and shape push the buttocks, thighs, hips, groins and muscles apart, resulting in a thigh gap being created and widening of the skeletal groin and muscles and hip region; which may also aid in the legs appearing more aligned. Furthermore, when buttocks cheeks and hips widen, they proportionally make the wearers waist look smaller, and thus they now have a shapelier, more desirable silhouette with a curvier bottom and waist section when the proportions are changed between the hips, buttocks, thighs, in comparison to the waist.

In one or more embodiments of the present disclosure, body shape enhancing apparatus 1 may comprise a substantially flat front section 2, yet ergonomically curved middle section 4, which may permanently connect to rear section 7 that may have a substantially sized protrusion 10 which may be any shape and or size and is at least a half inch high and half inch wide. The components of these embodiments may be detachably connected. The body shape enhancing apparatus 1 may be made of moldable and self-forming, adjusting textiles or fibers, or silicones or combination thereof, which may be enclosed by outer shell casing 3, which may be a single continuous outer shell casing 3 that is ergonomically engineered to fit the undercarriage of the wearer and capable of automatically cradling, hugging, and holding itself snuggly to the wearer's undercarriage without any internal components and having various cuts, widths, thickness and shapes. All features, coatings, oversleeves, adhesion means, garments, and or combination thereof, are available to this and any body shape apparatus 1 embodiment.

In one or more embodiments of the present disclosure, a method of using the body shape enhancing apparatus includes placing a front section 2 on a pelvic area of a wearer, wherein the front section 2 presses against wearers genitalia, in which it smooths the wearer's pelvic torso and conceals genital protrusion; placing a middle section 4 at about the perineum shaft, wherein the middle section is snuggly fit between the wearers lower inner thigh groins and expands the inner groins and hips aiding in separating the inner thighs 102 and 104 and placing protrusion 10 between the buttock's cheeks 70 and 72 of the wearer, wherein protrusion 10 lifts, separates, and firms buttocks by pushing them apart and effecting the capability of the wearer to create a thigh gap 105 beneath their undercarriage, buttocks cheeks, gluteal folds, and between their inner thighs 102 and 104.

It is understood that the thigh gap location zone of thigh gap 105, in which body shape enhancing apparatus 1 is capable of creating thigh gap 105 is beneath the wearer's undercarriage and buttocks cheeks, and between inner and thighs gluteal folds, directly under the perineum shaft.

Although the disclosure has been described by reference to illustrative embodiments thereof, many changes and modifications of the disclosure may become apparent to those skilled in the art without departing from the spirit and scope of the disclosure. It is therefore intended to include within this disclosure all such changes and modifications as may reasonably and properly be included within the scope of the present disclosure's contribution to the art. Benefits, other advantages and solutions to problems have been described above with regard to specific embodiments. However, the benefits, advantages, solutions to problems and any other element(s) that may cause any benefit, advantage or solution to occur or become more pronounced are not to be construed as critical, required or essential features or elements of any or all of the claims.

As used herein, the terms "comprise", "comprising" or any variation therefore, are intended to cover non-exclusive inclusion, such that a process, method, article, device or apparatus that comprises a list of elements does not include only those elements but may include other elements, boarder scope, alternative embodiments, mixture of, improvements not expressly listed or inherent to such processes, method, article, device, manufacture, or apparatus. Thus, the scope of the present disclosure is to be determined by the broadest permissible interpretation to the maximum extent allowed by law, of the following claims, and shall not be restricted or limited by the foregoing detailed description.

I claim:

1. A device adapted to cover exterior surfaces of a women's pelvic region extending from at least from a front of a women's vulva to a woman's anus, said device comprising:
    a top surface and a bottom surface wherein said bottom surface extends from a front end to a rear end of said device is shapeable and is shaped in a plane curve to conform to an exterior surface of a woman's pelvic region wherein said bottom surface is convex and said top surface is concave, said device further comprising,
    a front section, a middle section and a rear section, said front section comprising a planar body extending from said middle section,
    wherein said middle section extends between said front section and a rear section, and wherein said middle section has a dimension from a first side to an opposite second side and is comprised of a material that separates thighs of a woman and thereby creates a thigh gap; and said rear section comprises a protrusion that extends in a direction perpendicular to said bottom surface of said rear section.

2. The device as recited in claim 1 wherein said device is comprised of reusable material.

3. The device as recited in claim 1 wherein said device is self-supporting.

4. The device as recited in claim 1, wherein said top surface further comprises an antimicrobial material.

5. The device as recited in claim 1 wherein said device is comprised of an absorbent material.

6. The device as recited in claim 5 wherein said absorbent material is disposed on said top surface.

7. The device as recited in claim 5 wherein an exterior surface of said convex side is smooth.

8. A device adapted to cover a women's pelvic cavity and separate said women's thighs, wherein said device is sized and shaped to extend from at least a front of said women's vulva to said women's anus and further comprises:

a front curved planar section and a rear section, said rear section comprising a prism-shaped member, said prism-shaped member having a top surface that is flat, opposite side surfaces that extend from said top surface and said front curved planar section has a top surface that extends from said top surface of said rear section, and said front section has a larger lateral dimension than said rear section, wherein said rear section is adapted to separate thighs of a woman.

9. The device as recited in claim 8 further comprising means to hold said device against a women's body.

10. The device as recited in claim 8 further comprising straps wherein a first strap extends from a rear end of the device, and a second and third strap extend from a front end of said front section of the device.

11. The device as recited in claim 1 further comprising an absorbent material provided on said top surface.

12. The device as recited in claim 8 wherein said prism-shaped section is comprised of a material wherein when device is positioned on a woman's pelvis it separates thighs and buttocks of a woman and thereby creates or maintains a thigh gap.

13. The device as recited in claim 8 further comprising a flexible support member to allow said device to resiliently apply a restoring force against said woman's pelvic cavity and thereby engage said woman.

14. The device as recited in claim 8 incorporated into a garment.

15. The device as recited in claim 1 incorporated into a garment.

16. The device as recited in claim 1 wherein said front section is configured to conceal structure and appearance of a woman's vulva.

17. The device as recited in claim 8 wherein said front section is sized and shaped to conceal structure and appearance of a woman's vulva.

18. A method of shaping a women's body to increase a gap between a wearer's thighs comprising, wearing the device recited in claim 1 for a predetermined time period wherein said wearer's buttocks, groin, and legs are maintained apart by said device.

19. A device adapted to cover a portion of an exterior surface of a women's pelvic region, said region extending from a location in front of a woman's vulva to a location near a woman's anus, said device comprising:
 a concave top surface and a convex smooth bottom surface wherein said bottom surface extends from a front end to a rear end of said device and can be shaped in a plane curve to conform to an exterior surface of said pelvic region; said device further comprising, a front section, a middle section and a rear section, said front section comprising a planar body extending from said middle section, wherein said middle section extends between said front section and a rear section, and wherein said middle section is adapted to separate thighs of a woman and thereby create a thigh gap; and said rear section comprises a protrusion, wherein when worn by a woman, said protrusion separates buttocks cheeks of said woman and said protrusion extends in a direction perpendicular to said bottom surface of said rear section.

20. A method of using the device recited in claim 1 comprising applying said top surface of said device to a pelvic region wherein said device extends from a location in front of a vulva to a region between buttock's cheeks.

21. The device recited in claim 1, further comprising a biometric sensor.

22. The device as recited in claim 11 further comprising a bottom side made from an absorbent material.

23. The device recited in claim 1, wherein said device is comprised of biodegradable material.

24. The device recited in claim 1 wherein the rear section of said device has a lateral dimension wherein when said device is worn by a woman said lateral dimension maintains a space between a buttocks of said woman.

25. A device adapted to cover a women's pelvic cavity and separate thighs, wherein said device extends from at least a front of a vulva to a location near an anus comprising:
 a front flat planar curved section and a rear section, said rear section comprising a modified cylindrical shaped member, said modified cylindrical shaped member has a flat top surface and opposite side surfaces that meet together at a rounded bottom surface, wherein a top surface of said front flat planar curved section extends to said top surface of said rear section, and said front section has a larger lateral dimension than a lateral dimension of said rear section.

26. The device as recited in claim 25 wherein said modified cylinder is modified so that a portion of said side surfaces of said modified cylinder is flat.

27. The device as recited in claim 22 wherein said side walls are comprised an absorbent material.

28. The device as recited in claim 25 wherein said top surface and said side surface of said device comprises hypoallergenic material.

29. The device as recited in claim 1, wherein said a top surface further comprises a Cannabidiol polymer coating.

* * * * *